(12) United States Patent
Dadachova et al.

(10) Patent No.: US 11,058,666 B2
(45) Date of Patent: *Jul. 13, 2021

(54) ORAL ADMINISTRATION OF MELANIN FOR PROTECTION AGAINST RADIATION

(71) Applicant: ALBERT EINSTEIN COLLEGE OF MEDICINE, Bronx, NY (US)

(72) Inventors: Ekaterina Dadachova, Mahopac, NY (US); Arturo Casadevall, Pelham, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/433,169

(22) Filed: Jun. 6, 2019

(65) Prior Publication Data

US 2019/0298692 A1 Oct. 3, 2019

Related U.S. Application Data

(60) Division of application No. 15/230,617, filed on Aug. 8, 2016, now abandoned, which is a continuation of application No. 14/005,601, filed as application No. PCT/US2012/029213 on Mar. 15, 2012, now Pat. No. 9,408,882.

(60) Provisional application No. 61/454,242, filed on Mar. 18, 2011.

(51) Int. Cl.

| | |
|---|---|
| *A61K 36/06* | (2006.01) |
| *A61K 31/404* | (2006.01) |
| *A61K 31/05* | (2006.01) |
| *A61K 31/136* | (2006.01) |
| *A61K 31/198* | (2006.01) |
| *A61K 36/07* | (2006.01) |
| *A61K 9/00* | (2006.01) |

(52) U.S. Cl.
CPC .......... *A61K 31/404* (2013.01); *A61K 9/0095* (2013.01); *A61K 31/05* (2013.01); *A61K 31/136* (2013.01); *A61K 31/198* (2013.01); *A61K 36/06* (2013.01); *A61K 36/07* (2013.01)

(58) Field of Classification Search
None
See application file for complete search history.

(56) References Cited

U.S. PATENT DOCUMENTS

| | | |
|---|---|---|
| 5,227,459 A | 7/1993 | Pawelek et al. |
| 5,776,968 A | 7/1998 | Berliner et al. |
| 5,954,871 A | 9/1999 | Nicolas-Morgantini et al. |
| 9,408,882 B2 * | 8/2016 | Dadachova .......... A61K 31/198 |
| 2006/0052438 A1 | 3/2006 | Ho et al. |
| 2007/0237829 A1 | 10/2007 | Dadachova et al. |
| 2009/0328258 A1 | 12/2009 | Dadachova et al. |

FOREIGN PATENT DOCUMENTS

| | | |
|---|---|---|
| CN | 101317681 A1 | 12/2008 |
| EP | 761105 A1 | 3/1997 |

OTHER PUBLICATIONS

PCT International Search Report dated Jun. 22, 2012 in connection with PCT International Patent Application No. PCT/US2012/29213, 5 pages.
PCT Written Opinion of the International Searching Authority dated Jun. 22, 2012 in connection with PCT International Patent Application No. PCT/US2012/29213, 5 pages.
Japanese Office Action dated Dec. 24, 2015 in connection with Japanese Patent Application No. 2014-501148, 2 pages.
Zhu et al., entitled "Inhibition of quorum sensing in Chromobacterium violaceum by pigments extracted from Auricularia auricular," Letters in Applied Microbiology 52, 269-274, copyrighted 2011, revised 19 2010 and accepted Dec. 16, 2010, The Society for Applied Microbiology.

\* cited by examiner

*Primary Examiner* — Michael Barker
*Assistant Examiner* — Randall O Winston
(74) *Attorney, Agent, or Firm* — Cantor Colburn LLP

(57) ABSTRACT

Methods and compositions are provided for alleviating and/or preventing one or more side effects associated with exposure to radiation in a subject exposed to radiation or at risk for exposure to radiation comprising oral administration to the subject of an amount of an edible source of melanin effective to alleviate a side effect associated with radiation.

3 Claims, 16 Drawing Sheets

C)

D)

F)

G)

A

100/mg kg  stomach      small intestine    large intestine    liver      bone marrow 75/mg kg   stomach      small intestine    large intestine    liver      bone marrow 0/mg kg    stomach      small intestine    large intestine    liver      bone marrow

B

C

A

B

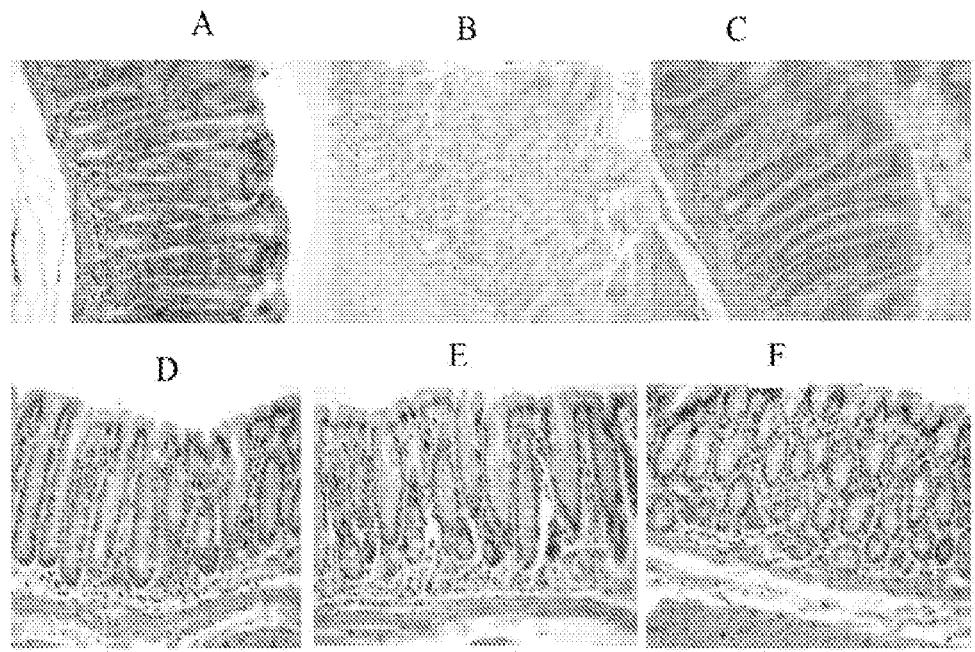
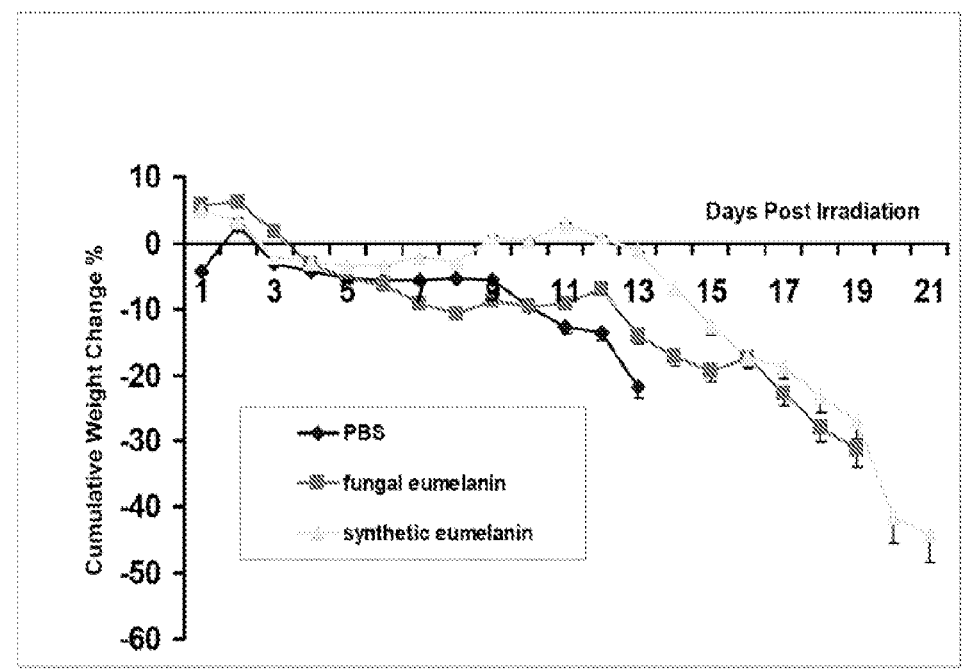
Fig. 9A-9G

ORAL ADMINISTRATION OF MELANIN FOR PROTECTION AGAINST RADIATION

CROSS-REFERENCE TO RELATED APPLICATIONS

This application is a divisional of U.S. patent application Ser. No. 15/230,617, which is a continuation of U.S. patent application Ser. No. 14/005,601, filed Oct. 15, 2013, now U.S. Pat. No. 9,408,882, issued Aug. 9, 2016, which is a U.S National Stage of PCT International Application No. PCT/US2012/029213, filed Mar. 15, 2012, which claims the benefit of U.S. Provisional Patent Application No. 61/454,242, filed Mar. 18, 2011, the contents of each of which are herein incorporated by reference in their entirety.

STATEMENT OF GOVERNMENT SUPPORT

This invention was made with government support under grant numbers AI-51519, AI087625, AI52733-07 and S10RR027308 awarded by the National Institutes of Health. The government has certain rights in the invention.

FIELD OF THE INVENTION

The present invention relates to use of melanin-containing substances, such as black mushroom-based food supplements, for oral administration for alleviating side effects associated with exposure to radiation such as ionizing radiation.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Melanin is a high molecular weight pigment that is ubiquitous in nature and has a variety of biological functions (5). Melanins are found in all biological kingdoms. These pigments are among the most stable, insoluble, and resistant of biological materials (6). Melanins can have different structures depending on the biosynthetic pathway and precursor molecules. Some definitions of melanin have focused on chemical and physical properties of melanins instead of defined structures (7). Melanins can be synthesized in the laboratory by chemical means or by many living organisms. Melanins formed by the oxidative polymerization of phenolic compounds are usually dark brown or black (6). However, melanins may have other colors as illustrated by the finding that dopamine-derived melanin is reddish-brown. Fungi can make melanins from at least two major biosynthetic pathways, employing the precursor 1,8-dihydroxynapthalene (DHN melanin) or the oxidation of suitable tyrosine derivatives like dihydroxyphenylalanine (DOPA-melanin) (6). The fungus C. neoformans can make melanins from a wide variety of phenolic compounds which are oxidized by a laccase enzyme (8-10). Many fungi constitutively synthesize melanin (11).

Every year 1.4 million people are diagnosed with cancer in the U.S. and half of them will undergo some form of radiation therapy in the course of their disease. The availability of radioprotective compounds would alleviate the morbidity associated with the radiation exposure. The doses received by millions of patients during diagnostic radiological procedures are also very high (the dose of a multi-slice cardiac CT scan is equal to the dose from 300 chest X-rays) and are of great concern as well; thus such patients would also benefit from the affordable and effective radioprotectors. There is also importance for public safety to have radioprotective agents readily available in the event of a nuclear accident or terrorist attack.

Radioprotective agents that could be given prior to, or even during, radiation exposure would be of significant value in alleviating the side effects associated with exposure to ionizing radiation. Currently there are no FDA-approved radioprotectors. It would be extremely beneficial for hundreds of millions of people to have access to food supplements that could fill the niche in the absence of radioprotective drugs.

Fungal melanins can function as energy transducing molecules capable of capturing high energy electromagnetic radiation and converting it into an energy form that is useful to fungal cells (1). Furthermore, fungal melanins can be effective shields against radiation; the efficacy of radioprotection by melanins is dependent on their chemical composition and spatial arrangement (2). In addition to free reactive radical scavenging, radioprotection by melanins involves prevention of free radical generation by Compton recoil electrons through gradual recoil electron energy dissipation by the $\pi$-electron-rich melanin until the kinetic energy of recoil electrons becomes low enough to be trapped by stable free radicals present in the pigment (3). It has also been shown that melanin-based nanoparticles protect bone marrow in mice subjected to external whole body radiation or radioimmunotherapy (4).

The present invention addresses the need for radioprotectants in humans at risk for radiation exposure using melanin-based products.

SUMMARY OF THE INVENTION

The invention provides methods for alleviating and/or preventing one or more side effects associated with exposure to radiation in a subject exposed to radiation or at risk for exposure to radiation comprising oral administration to the subject of an amount of an edible source of melanin effective to alleviate a side effect associated with radiation.

The invention also provides a method for increasing the survival rate of a plurality of subjects exposed to an amount of radiation likely to kill the plurality of subjects, comprising oral administration to each of the plurality of subjects of an amount of an edible source of melanin effective to increase the survival rate of the plurality of subjects exposed to the amount of radiation likely to kill the plurality of subjects.

The invention also provides edible sources of melanin packaged for oral administration to a subject for alleviating and/or preventing one or more side effects associated with exposure of the subject to radiation, wherein the edible source provides melanin in an amount equivalent to at least 8 mg of purified melanin per kg of body weight of the subject.

The invention also provides a drinkable suspension of melanin packaged for oral administration to a subject for alleviating and/or preventing one or more side effects associated with exposure of the subject to radiation, wherein the drinkable suspension comprises at least 500 mg melanin in a volume of 500 mL or less.

BRIEF DESCRIPTION OF THE FIGURES

FIG. 9A-9H. Radiation effects in CD-1 mice fed with 15 mg/kg body weight microbial or synthetic eumelanin and irradiated with 9 Gy gamma radiation at 2.5 Gy/min: (a-f) histology of GI tract tissues obtained from irradiated CD-1 mice sacrificed at 4 hr (a-c) and at 24 hr (d-f) post-irradiation: a) stomach, synthetic eumelanin group; b) stomach, microbial eumelanin group; c) stomach, PBS. Fewer apoptotic cells are seen in stomach tissue of microbial melanin fed mice than in synthetic eumelanin or PBS groups; d) colon, synthetic eumelanin group; e) colon, microbial eumelanin group; f) colon, PBS control group; g) cumulative weight loss in CD-1 mice; h) survival of the irradiated mice. Original magnification ×400.

DETAILED DESCRIPTION OF THE INVENTION

Figure 1:
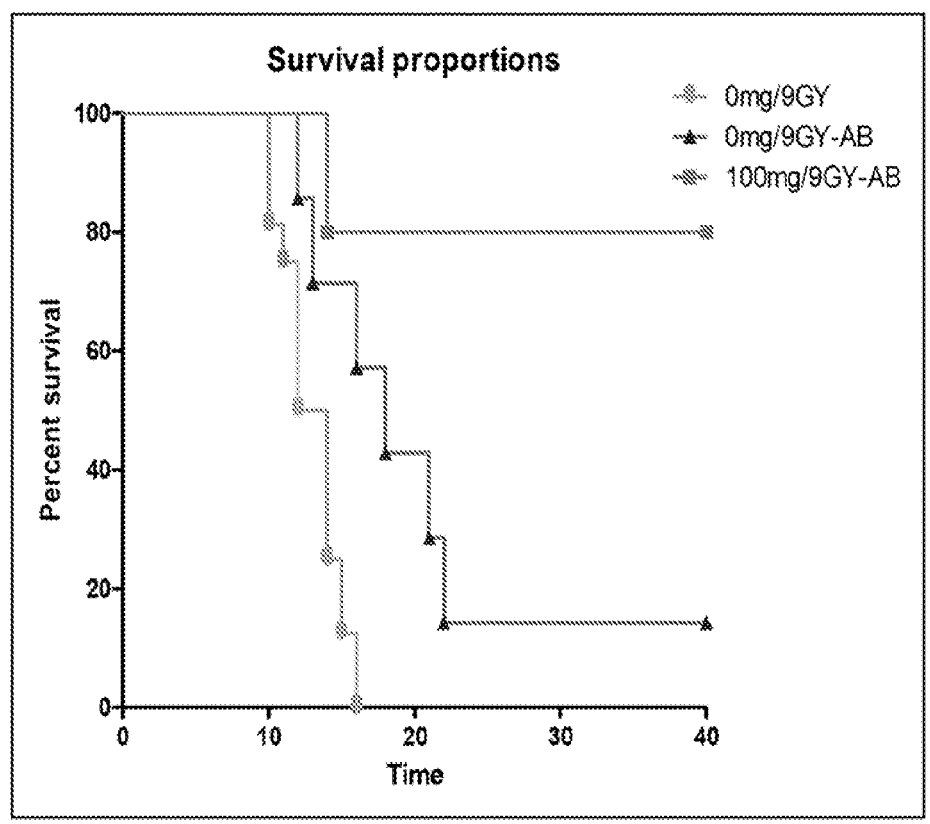
FIG. 1. Survival of CD1 mice receiving synthetic pheomelanin before 9 Gy whole body radiation dose. Three hours before receiving the whole body dose of 9 Gy, the mice were given by oral gavage either 100 mg/kg body weight synthetic pheomelanin followed by 5 days of antibiotic support, or PBS followed by 5 days of antibiotic support, or PBS alone. AB—antibiotic support. 10 mice per group were used. P values were 0.001 and 0.002 when the survival in pheomelanin group was compared with PBS and PBS plus antibiotics groups, respectively.

The invention provides a method for alleviating one or more side effects associated with exposure to radiation in a subject exposed to radiation or at risk for exposure to radiation comprising oral administration to the subject of an amount of an edible source of melanin effective to alleviate a side effect associated with radiation.

The invention also provides a method for increasing the survival rate of a plurality of subjects exposed to an amount of radiation likely to kill the plurality of subjects, comprising oral administration to each of the plurality of subjects of an amount of an edible source of melanin effective to increase the survival rate of the plurality of subjects exposed to the amount of radiation likely to kill the plurality of subjects. One skilled in the art will know from then literature the amount of radiation likely to kill the plurality of subjects. For example, for human beings the $LD_{50/60d}$ (i.e. the dose that causes 50% mortality with 60 days of exposure) in humans from acute, whole body radiation exposure is in excess of 250 rad (2.5 Gy) and usually approximately 400 to 500 rads (4-5 Gy).

Preferably, melanin is administered to the subject in an amount equivalent to at least 8 mg of purified melanin per kg of body weight of the subject. For example, melanin can be administered in an edible substance, containing at least 10% melanin by dry weight, of at least 80 mg of edible substance per kg of body weight of the subject. For example, melanin can be administered as at least 80 mg of dry mushrooms per kg of body weight of the subject, where the mushrooms contain at least 10% melanin by dry weight. In an embodiment, the melanin is administered in the form of a drinkable suspension. In an embodiment, the edible source of melanin comprises a drinkable suspension of melanin packaged for oral administration to a subject for alleviating and/or preventing one or more side effects associated with exposure of the subject to radiation, wherein the drinkable suspension comprises at least 500 mg melanin in a volume of at least 10 mL.

The invention also provides an edible source of melanin packaged for oral administration to a subject for alleviating and/or preventing one or more side effects associated with exposure of the subject to radiation, wherein the edible source provides melanin in an amount equivalent to at least 8 mg of purified melanin per kg of body weight of the subject. In an embodiment, the edible source provides melanin in an amount equivalent to at least 9, 10, 15 or 20 mg of purified melanin per kg of body weight of the subject.

The invention also provides a drinkable suspension of melanin packaged for oral administration to a subject for alleviating and/or preventing one or more side effects associated with exposure of the subject to radiation, wherein the drinkable suspension comprises at least 250 mg melanin in a volume of at least 10 mL. In an embodiment, the drinkable suspension comprises at least 500 mg melanin in a volume of at least 10 mL. In an embodiment, the drinkable suspension comprises at least 560 mg melanin in a volume of at least 10 mL. In an embodiment, the drinkable suspension comprises the melanin in at least 25 mL, 50 mL, 75 mL, 100 mL, 125 mL, 150 mL, 175 mL, 200 mL, 250, mL, 500 mL or 750 mL. In an embodiment, substantially all the melanin is in particulate form or smaller. The drinkable suspension can be galenical.

The invention also provides a powderized form of melanin packaged for making a drinkable suspension by dilution with a drinkable liquid. The powderized form of melanin may be packaged, for example in a sachet. In an embodiment, the powderized form of melanin is formulated so as to permit, upon reconstitution with at least 10 mL, 25 mL, 50 mL, 75 mL, 100 mL, 125 mL, 150 mL, 175 mL, 200 mL, 250, mL, 500 mL or 750 mL a drinkable suspension providing at least 8 mg of purified melanin per kg of body weight of the subject who will drink the drinkable suspension. In an embodiment, the powderized form of melanin is formulated so as to permit, upon reconstitution with at least 10 mL, 25 mL, 50 mL, 75 mL, 100 mL, 125 mL, 150 mL, 175 mL, 200 mL, 250, mL, 500 mL or 750 mL a drinkable suspension providing at least 250 mg, 500 mg or 560 mg melanin.

The melanin can be isolated or derived from a melanin-containing biological source where melanin constitutes at least 10% of the dry weight of the biological source. Melanin can also be synthesized chemically. Melanin can also be provided by administering a melanin-containing biological source that comprises at least 10% melanin per dry weight of the biological source. In an embodiment, the melanin is in a composition substantially free of fungal material.

The biological source can be, for example, a melanin-containing plant, cell, fungus or microorganism such as a bacterium. Preferred fungi include melanin-containing edible mushrooms, such as *Auricolaria auricular-judae* or *Pleuroyus cystidiosus*. A chemical source for melanin can be auto- or catalytic-polymerization of certain phenolic compounds like L-dopa.

The biological source can be grown in the presence of a melanin precursor, such as, for example, one or more of L-dopa (3,4-dihydroxyphenylalanin), D-dopa, catechol, 5-hydroxyindole, tyramine, dopamine, tyrosine, cysteine, m-aminophenol, o-aminophenol, p-aminophenol, 4-aminocatechol, 2-hydroxyl-1,4-naphthaquinone, 4-metholcatechol, 3,4-dihydroxynaphthalene, gallic acid, resorcinol, 2-chloroaniline, p-chloroanisole, 2-amino-p-cresol, 4,5-dihydroxynaphthalene, 1,8-dihydroxynaphthalene, 2,7-disulfonic acid, o-cresol, m-cresol, and p-cresol.

The melanin can comprise allomelanin, pheomelanin and/or eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. In one embodiment, the ratio of pheomelanin to eumelanin is at least 1:1. Preferably, the melanin contains divalent sulfur.

Preferably, one or more internal organs of the subject are protected from radiation. Preferably, the organ that is protected is one or more organ selected from the group consisting of bone marrow, liver, spleen, kidneys, lungs, and gastrointestinal tract.

The side effect associated with radiation can be one or more of nausea, vomiting, abdominal pain, diarrhea, dizziness, headache, fever, cutaneous radiation syndrome, low blood cell count, infection due to low white blood cells, bleeding due to low platelets, anemia due to low red blood cells, or death. Preferably, the subject's chance of survival is increased following exposure to radiation. In one embodiment, the dose of radiation received by the subject would be lethal to the subject in the absence of radioprotection.

The subject can be any animal. Preferably the subject is a mammal and more preferably a human.

The radiation can comprise ionizing radiation. Ionizing radiation is of sufficiently high energy that it ionizes atoms. The radiation can be, for example, one or more of gamma radiation, x-ray radiation, bremsstrahlung radiation, ultraviolet radiation, and particulate radiation (e.g., α-radiation and β-radiation). The source of the radiation can be a medical isotope. In a preferred embodiment the ionizing radiation is gamma radiation, α-radiation or β-radiation. In an preferred embodiment, the radiation is from a man-made source of radiation. For example, the source of the radiation can be radiation therapy used for treatment of disease (such as radiotherapy), radiation from a medical imaging device (such as a CT scanner), radiation used for radiation surgery (e.g. stereotactic radiation surgery), a nuclear weapon, or a nuclear reactor, such as a nuclear reactor in a power plant or submarine or high-altitude radiation, e.g. as experienced in commercial or military flights or space flight. In an embodiment, the high-altitude radiation is natural ionizing radiation experienced at altitudes in excess of 20,000 ft. The source of radiation can result from a terrorist attack. Thus, a man-made source of radiation can include that resulting from natural radioactive isotopes, but as applied in a man-made therapy, power source or device.

Subjects expected to benefit from the present invention include, but are not limited to, the following. Every second patient in the U.S. who is diagnosed with cancer (1.4 million people per year are diagnosed in the U.S.) will undergo some form of radiation therapy during the course of their disease. Another group of patients who will benefit are those who undergo CT (computer tomography) scans. 72 million CT scans are performed in the U.S. every year. There is growing concern about high doses of radiation that many patients receive during those scans, which are often recommended for them several times per year. The dose from one high resolution cardiac multi-slice CT scan is equivalent to approximately 100-600 chest X-rays or over 3-years' worth of natural background radiation. Yet another group of patients who can benefit from the present invention are people undergoing so-called stereotactic radiosurgery (done with Particle beam (proton)), or Cobalt-60 based (photon), or linear accelerator-based for conditions such as arteriovenous malformations, benign brain tumors, and functional disorders including trigeminal neuralgia, essential tremor, and Parkinson's tremor/rigidity. Additional subject who could benefit from the present invention are frequent fliers and airline personnel whose doses are known to exceed the annual limit for radiation occupational workers, nuclear medicine and radiology professionals, personnel at the nuclear power plants and nuclear reactors, and military personnel in nuclear submarines, as well as victims of radiation accidents and terrorist attacks.

In an embodiment of the methods, the treatment results in reducing the likelihood that the exposed subject will develop a cancer as a result of chronic radiation exposure over an extended time period.

Melanin could be provided in the form of dry black mushrooms suspended in palatable liquid ("melanin shakes"). The mushroom that could be used include black edible mushrooms such as *Auricularia auricular-judae*. Mushrooms such as *Auricularia auricular-judae* can be grown as other edible mushrooms in a basement of a building when provided with humidity and nutrients, dried, powderized and formulated into "melanin shakes" by mixing it with flavored water or fruit juice. Shakes with different flavors can be made. The packaging can be standard individual juice cartons, e.g. 100 mL volume. Melanin could also be provided in other edible forms, e.g., melanin brownies. Alternatively, naturally occurring or synthetic melanins can be isolated or synthesized, respectively, and added to foodstuffs to create products suitable for oral ingestion. In non-limiting embodiments, the melanin from black mushrooms can be processed so as to be particulate or powderized. In an embodiment, the melanin is from an organism, such as a fungi, which has been exposed itself to radiation in an amount effective to increase the melanin production in the organism (radiosynthesis). In an embodiment, the organism has been grown under conditions comprising the presence of a melanin precursor. Methods for both radiosynthesis and growing in the presence of a melanin precursor are described in U.S. Patent Application Publication No. US 2009-0328258 A1, published Dec. 31, 2009, which is hereby incorporated by reference.

Also provided is a drinkable suspension of melanin packaged for oral administration to a subject for alleviating and/or preventing one or more side effects associated with exposure of the subject to radiation, wherein the drinkable suspension comprises at least 500 mg melanin in a volume of at least 10 mL. In an embodiment, the drinkable suspension comprises at least 500 mg melanin in a volume of at least 100 mL.

In an embodiment, the subject has been, is being, or will be exposed to a single radiation exposure of 10 mGy, 20 mGy, 50 mGy, 100 mGy, 500 mGy, 1 Gy, 1.5 Gy, 2 Gy or greater, 5 Gy or greater, 7.5 Gy or greater, 10 Gy or greater or greater than 10 Gy. In humans, a whole-body exposure to 5 or more Gy of high-energy radiation at one time usually leads to death within 14 days.

In embodiments of the methods and compositions, including suspensions, the melanin is not in the form of melanized nanoparticles.

In an embodiment, the methods further comprise administering one or more antibiotics to the subject.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Radiation protection with synthetic melanin: The radioprotective properties of fungal and synthetic melanins were tested by oral administration of synthetic pheomelanin to mice before whole body exposure to 1.5 lethal dose (9 Gy) of gamma radiation. The whole body dose of 9 Gy is also 2.5 times the lethal dose for a human. The resulting survival of mice protected with melanins (FIG. 1) provided encouragement for the use and development of melanin-based products as radioprotectants in humans at risk for radiation exposure.

Figure 2:
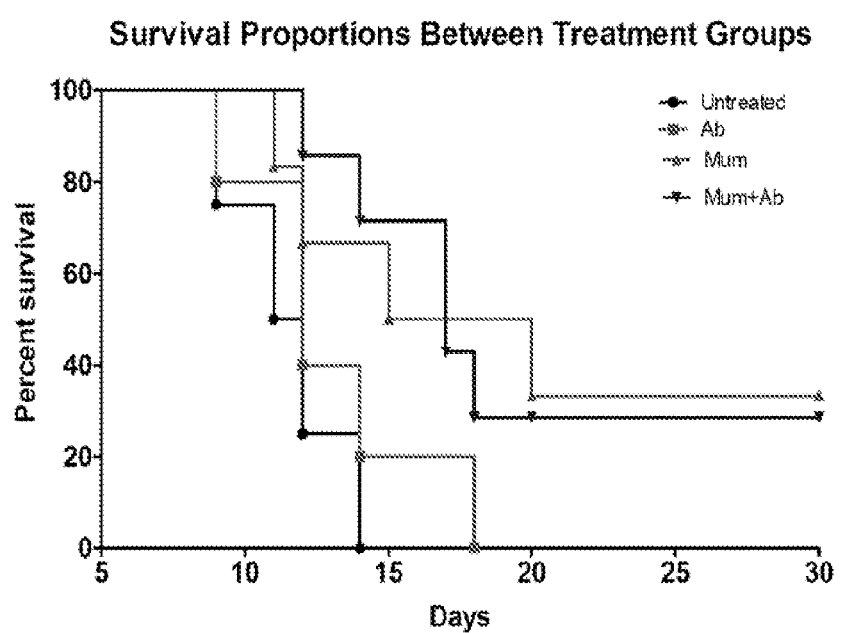
FIG. 2. Survival of CD1 mice after 9 Gy whole body radiation dose. Three hours before receiving the whole body dose of 9 Gy the mice were given by oral gavage either 1 g/kg body weight of *Auricolaria judae* mushroom suspended in PBS, or 1 g/kg body weight of *Auricolaria judae* mushroom followed by antibiotics support for 5 days, or PBS followed by antibiotics support for 5 days, or PBS alone. There were 5 mice in PBS alone and in PBS plus antibiotic support groups, and 6 mice in mushrooms and mushrooms plus antibiotics groups. The P value was 0.015 for both mushrooms and mushrooms plus antibiotics when compared to PBS alone and to PBS plus antibiotics controls. Ab—antibiotics support, Mum—mushrooms.

Radiation protection with black edible mushrooms: In a follow-up experiment, it was investigated whether the result with synthetic melanin would apply to natural melanins. The edible fungus *Auricularia auricular-judae* was selected since it is heavily melanized. Three hours before receiving the whole body dose of 9 Gy, groups of 5-6 CD1 mice were given by oral gavage 1 g/kg body weight of *Auricularia auricular-judge* mushroom suspended in PBS, or 1 g/kg body weight of *Auricularia auricular-judae* mushroom followed by antibiotics support for 5 days after irradiation, or PBS followed by antibiotics support for 5 days after irradiation, or PBS alone. Mice were monitored for their survival for 30 days since in radioprotection experiments mice are considered to be surviving indefinitely beyond that point. The results of the experiment are shown in FIG. 2. Black mushroom *Auricularia auricular-judae* significantly prolonged the survival of lethally irradiated mice, with 30% of mice given mushrooms alone or mushrooms with antibiotic support surviving for 30 days. There were 5 mice in PBS alone and in PBS plus antibiotic support groups, and 6 mice in mushrooms and mushrooms plus antibiotics groups. The P value was 0.015 for both mushrooms and mushrooms plus antibiotics when compared to PBS alone and to PBS plus antibiotics controls.

Given that synthetic melanins and melanin in microscopic fungi have a similar structure as the melanin found in edible mushrooms, a food supplement could be used to supply melanin in the form, for example, of dry black mushrooms suspended in palatable liquid ("melanin shakes") to individuals to be subjected to radiation exposure. In studies with oral administration of melanin the protective dose of purified melanin was 100 mg/kg in a mouse, which will be 8 mg/kg purified melanin in a human taking into consideration the different weight to body surface area ratios in mice and humans. Provided that melanin constitutes at least 10% of a dry mushroom weight—in a mouse experiment described above, mice received 1 g/kg of *Auricularia auricular-judae* which in a human will be equal to 80 mg/kg of dry mushrooms, or 5.6 g per 70 kg person. *Auricularia auricular-judae* can be grown as other edible mushrooms in a basement of a building when provided with humidity and nutrients, dried, powderized and formulated into "melanin shakes" by mixing it with flavored water or fruit juice.

Shakes with different flavors can be made. The packaging can be standard individual juice cartons, e.g. 100 mL volume.

Example 2

Figure 3A:
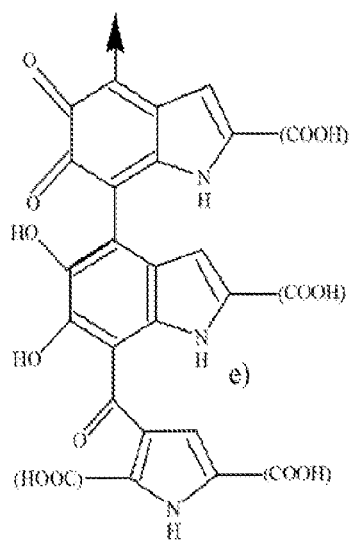
FIG. 3A-3E. Chemical composition of melanins and appearance of melanins from various sources and mushrooms used in the study: a) structure of eumelanin oligomer; b) structure of pheomelanin oligomer; c) electron micrograph of purified microbial melanin (melanin "ghosts"); d) synthetic melanin—eumelanin (black) on the left and pheomelanin (brown) on the right; e) edible mushrooms used in the study—*Boletus edulis* (white mushrooms) on the left and *Auricularia auricula-judae* (black mushrooms) on the right.
Figure 3B:
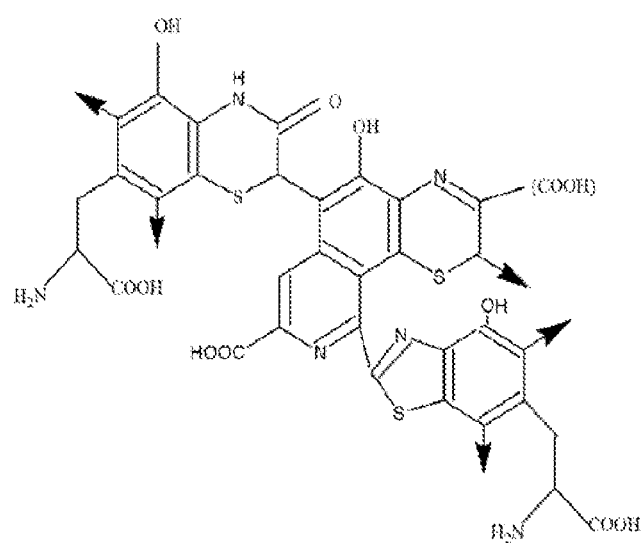
Figure 3C:
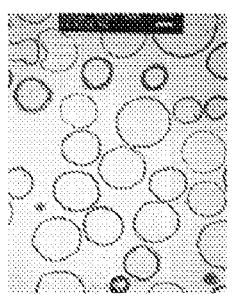
Figure 3D:
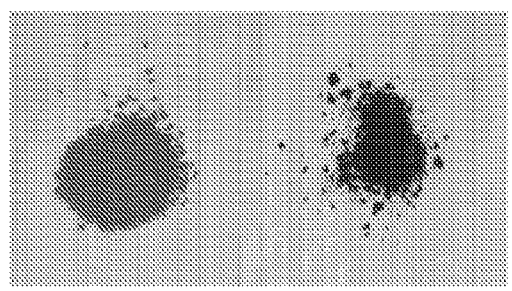
Figure 3E:
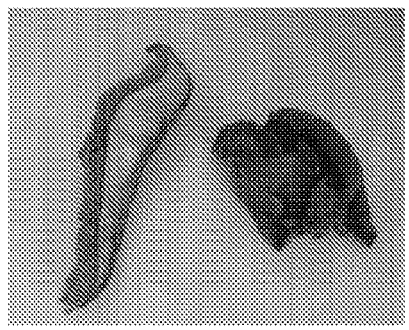
Figures 4A, 4B:
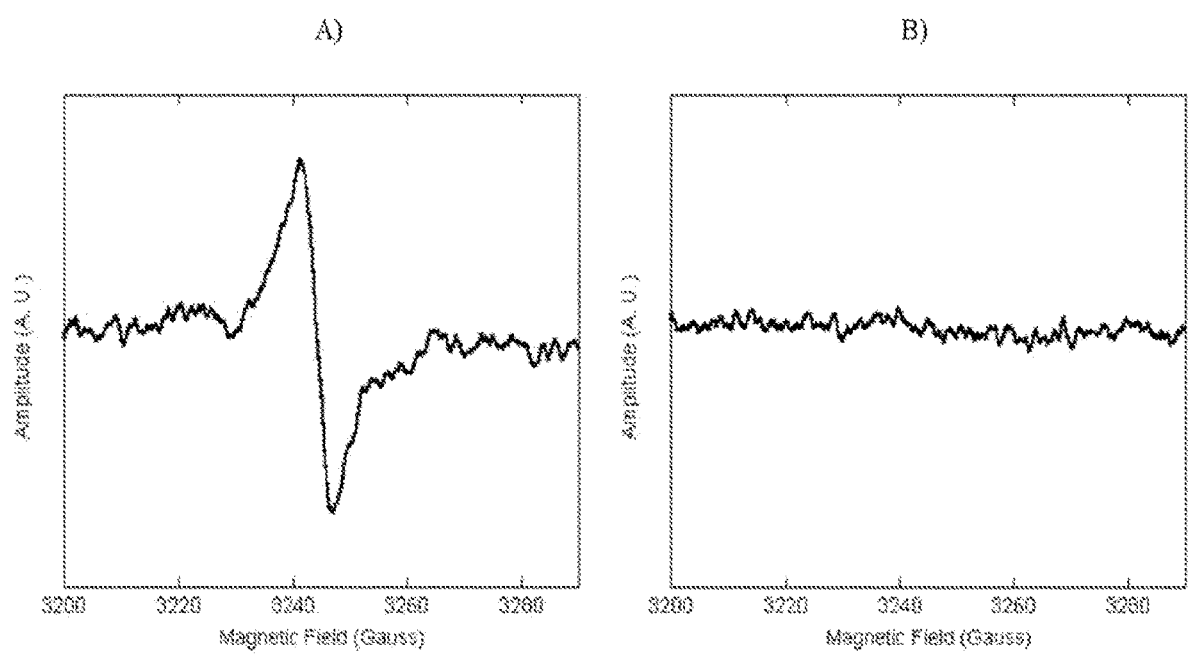
FIG. 4A-4G. Physico-chemical characterization of black and white mushrooms: a, b) EPR of dried mushrooms: a) black mushrooms; b) white mushrooms; c-e) oxidative HPLC of melanin purified from black mushrooms: c) background solution; d) PDCA standard eluting at 8 min.; e) melanin from black mushrooms showing PDCA peak; f, g) results of DPPH assay for antioxidant presence: f) butylated hydroxyanisole (BHA) positive control; g) methanol extracts from black and white mushrooms.
Figure 4C:
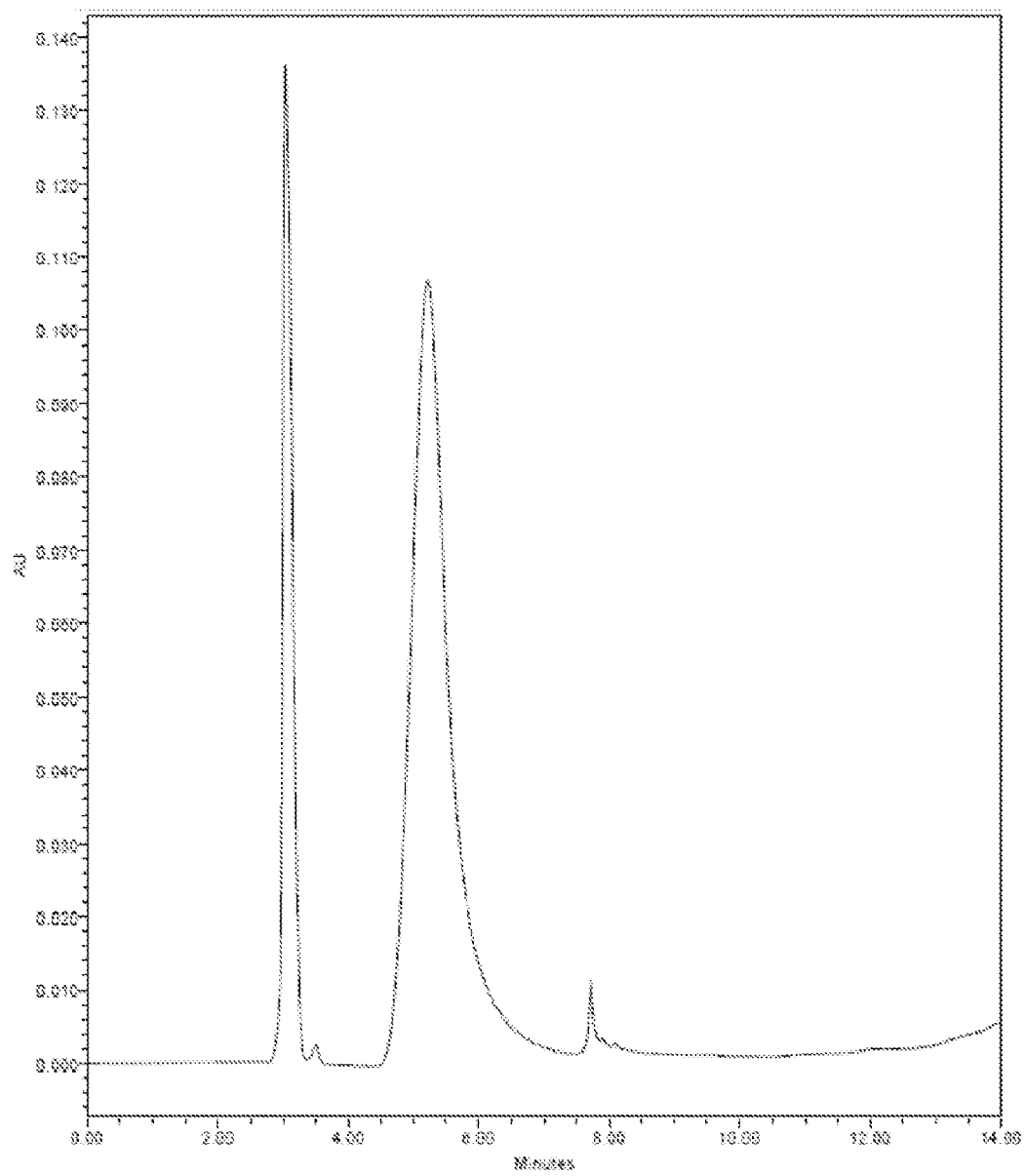
Figure 4D:
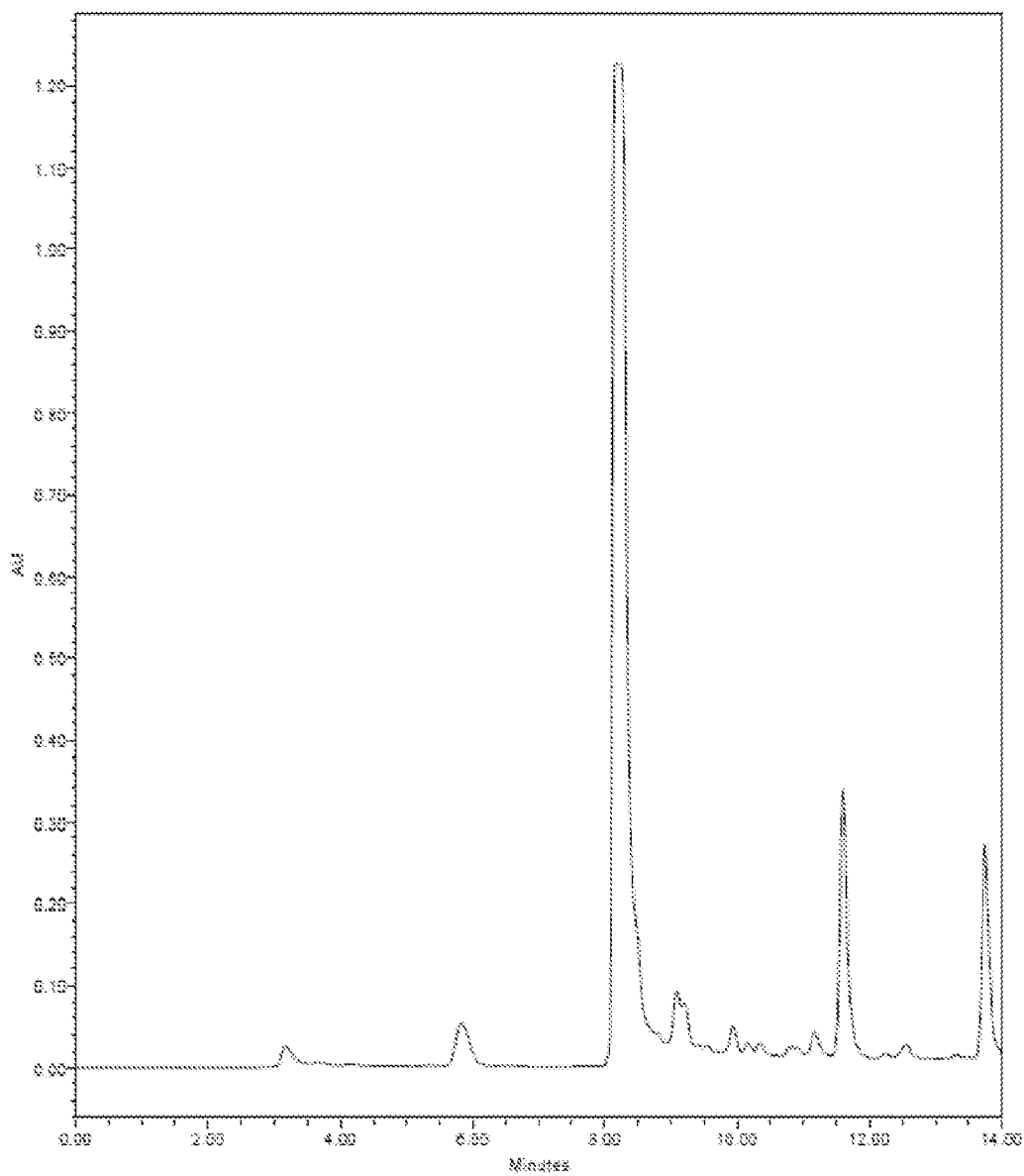
Figure 4E:
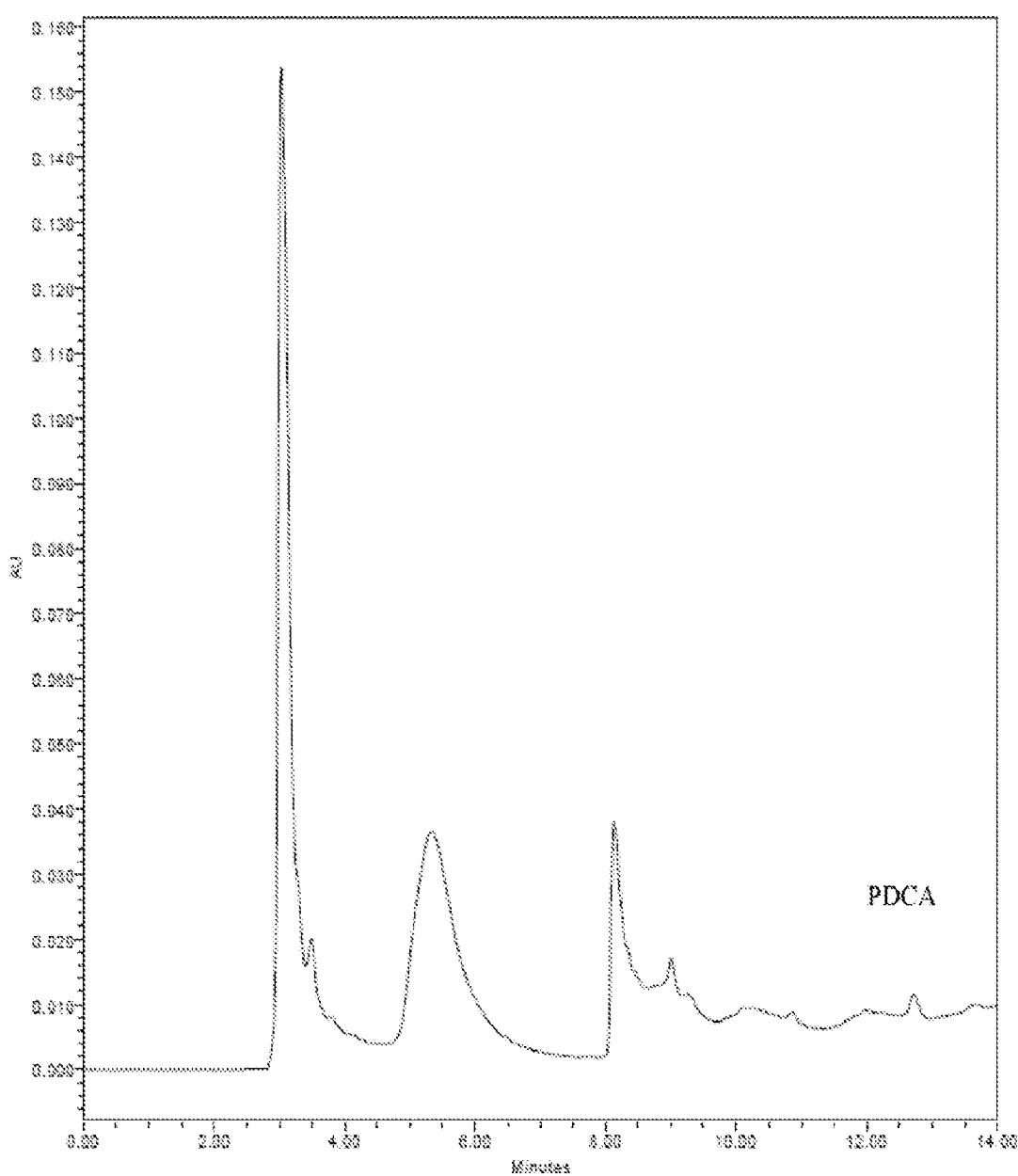
Figure 4F:
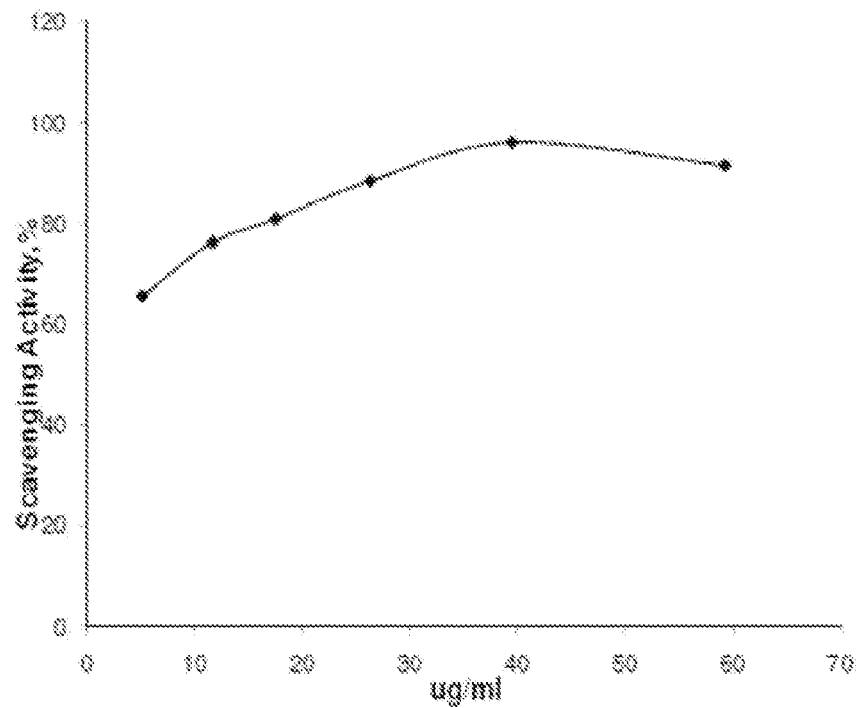
Figure 4G:
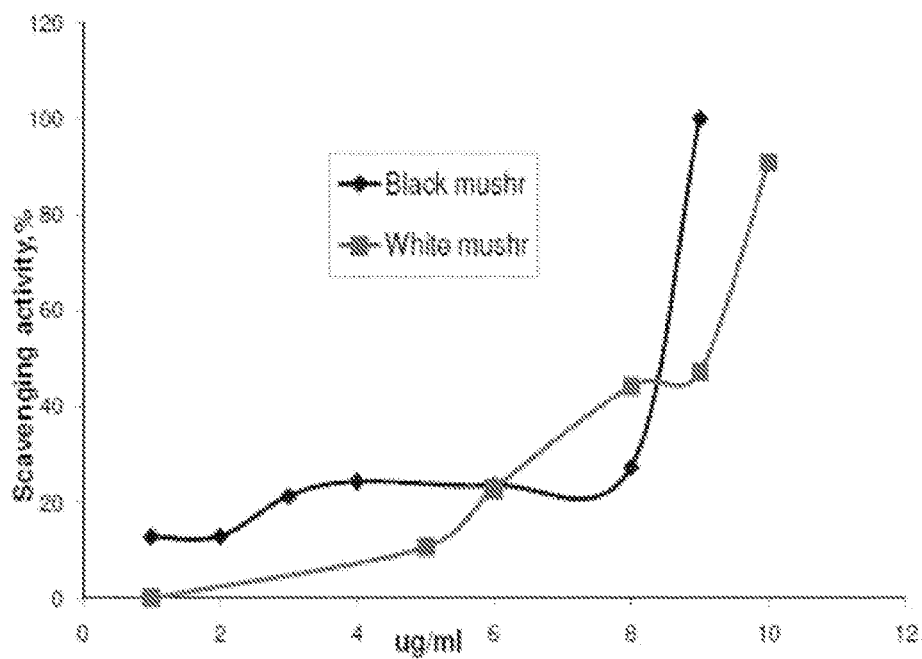

Melanin-containing edible mushrooms offered the highest degree of radioprotection without antibiotic support. The radioprotective efficacy of melanin delivered as a natural food source was evaluated. The black edible mushroom *Auricularia auricula-judae* (common names Jelly Ear or Judas Ear) was selected as a source of edible melanin and the white mushroom *Boletus edulis* (common names porcino or bun bun) as a melanin-devoid control (FIG. 3E). Both types of mushroom are basidiomycetes that are used in Western and Asian cuisines and are available commercially in dried form. The presence of melanin in *Auricularia auricula-judae* (black mushrooms) and its absence in *Boletus edulis* (white mushrooms) was demonstrated by electron paramagnetic resonance (EPR) with characteristic melanin "signature" signal in black mushrooms (FIG. 4A) and background only—in white mushrooms (FIG. 4B). Melanin purified from black mushrooms using the protocol developed in our laboratories (19) constituted approximately 10% of black mushrooms dry weight and was further characterized by elemental analysis and oxidative high performance liquid chromatography (HPLC). Eumelanins are composed of 5,6-dihydroxyindole (DHI) and 5,6-dihydroxyindole-2-carboxylic acid (DHICA) monomer units with 6-9% nitrogen (20, 21). In parallel, fungi also synthesize eumelanin from 1,8-dihydroxynaphthalene (DHN) via pentaketide synthetic pathway and such melanin does not contain nitrogen in its structure (22). The elemental analysis determined that there was 44% carbon, 5% hydrogen and 2% nitrogen in black mushroom melanin. The low percentage of nitrogen suggested that the pigment was primarily DHN-melanin, while the HPLC of oxidized melanin gave additional information about its structure (FIG. 4C-E). The presence of pyrrole-2,3-dicarboxylic acid (PDCA), which is an oxidation product of DHI-derived units in oxidized melanin allowed a conclusion that melanin in black mushrooms was a mixture of DHN and DHI melanins. In addition, it was considered whether mushroom-associated antioxidants could contribute to the radioprotective effect and compared the antioxidant contents of black and white mushrooms using 2,2-diphenyl-1-picrylhydrazyl (DPPH) assay. The DPPH is a stable free radical having a deep violet color in solution. The radical scavenging activity of a sample can be measured as a decolorizing effect following the trapping of the unpaired electron of DPPH12. There was no difference in soluble antioxidant content between black and white mushrooms (FIG. 4F, 4G), thus excluding differences in antioxidants as the basis of black mushroom-mediated radiation protection in vivo. It is important to note, that only soluble antioxidants are measured in this assay as they are extracted into methanol. Melanin which also possesses powerful free radical scavenging properties by virtue of being a stable free radical (24) cannot contribute to the results of this assay as it is not soluble in methanol or any other common solvents.

Figure 5A:
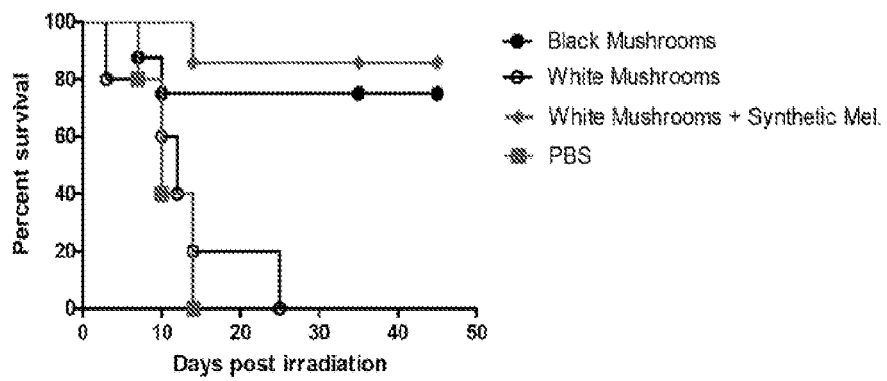
FIG. 5A-5H. Survival of irradiated CD-1 mice fed with black edible mushrooms, blood counts in the surviving mice and histology of the GI tract and bone marrow. Mice were divided into groups of 5-6 and fed 1 g/kg body weight black mushroom suspension in PBS, or PBS alone, or 1 g/kg white mushroom suspension, or 1 g/kg white mushroom suspension supplemented with 100 mg/kg synthetic melanin via gavage needle. One hour after mushroom administration mice were irradiated with 9 Gy dose of Cs-137 radiation at a dose rate of 2.5 Gy/min. a) Kaplan-Meyer survival curves. The experiment was performed twice and was terminated at day 45; b) white blood cells counts; c) platelet counts; d-h) H&E stained slides with tissues from control and irradiated mice. Left, non-irradiated controls; middle, black mushroom group; right, white mushroom supplemented with melanin. d) stomach, magnification ×400; e) LI, magnification 400; f) SI, magnification ×200; g) bone marrow, magnification ×400; h) spleen, magnification ×100.
Figure 5B:
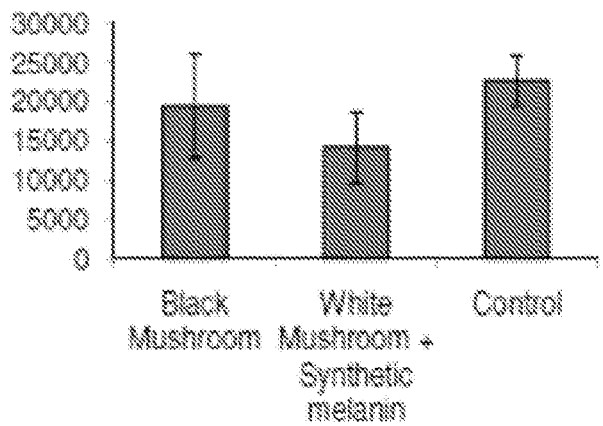
Figure 5C:
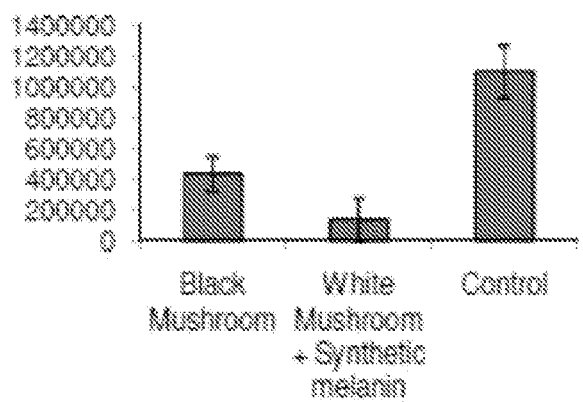
Figures 5D, 5E, 5F, 5G, 5H:
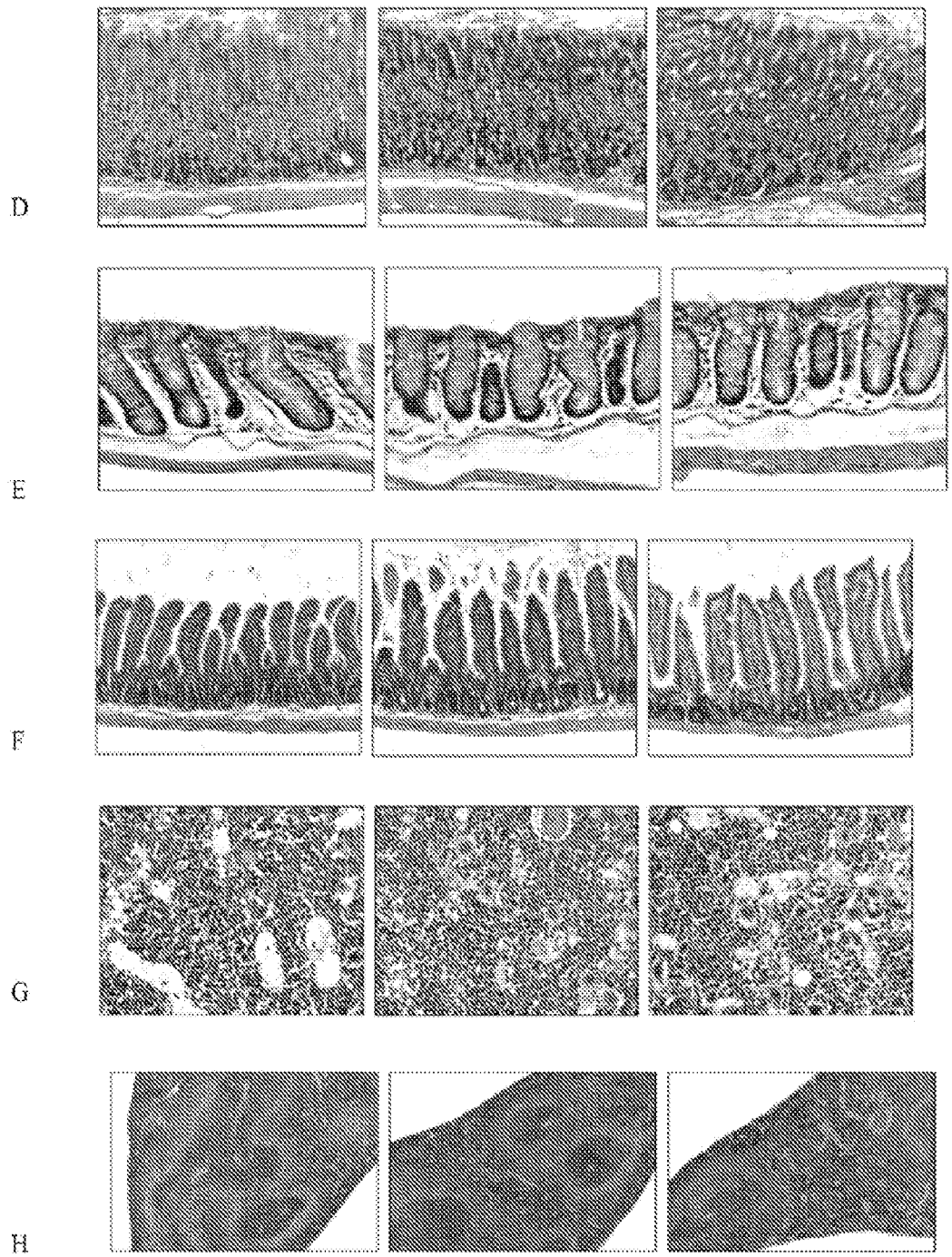

To test the radioprotective properties of edible mushrooms in mice we first need to determine the time between feeding mice with mushrooms and irradiation to ascertain the presence of mushrooms in GI tract during irradiation. The fluorescent imaging was performed by utilizing the natural autofluorescence of white mushrooms. Mice were given mushroom suspension with a gavage needle and imaged on IVIS Spectrum Imaging System at 15, 30 and 60 min post-feeding. 675/30 nm and 840/20 nm filters were used for excitation and emission, respectively. Mice were given 1 g/kg body weight white mushrooms suspension in water via gavage needle and imaged in supine position under Isoflurane anesthesia. The mushrooms were in the stomach at 15 and 30 min post-feeding and moved into the intestines to the large extent at 60 min (data not shown). As intestines are more sensitive to ionizing radiation than stomach, we selected 60 min as time to administer radiation in order to ensure maximum protection for the most sensitive part of GI tract. Armed with these results, we conducted a radioprotection study in mice given lethal whole body dose of 9 Gy. Groups of 5-6 CD-1 mice were used in the experiment which was then repeated with the similar results. Black mushrooms were administered as suspension in sterile PBS via gavage as 1 g/kg body weight. The control groups included mice given only sterile PBS, or white mushrooms as 1 g/kg body weight dose. To establish that the melanin pigment was indeed the radioprotective substance in black mushrooms an additional group of mice was given white mushrooms as 1 g/kg body weight dose supplemented with 100 mg/kg of synthetic melanin dosed to match its contents in black mushrooms. All mice in the PBS group and 80% in the white mushrooms—fed group died by day 14 post irradiation (FIG. 5A). The remaining 20% of mice in the white mushroom-treated group died by day 25. This trend toward prolongation in survival in comparison with PBS alone group which was not statistically significant (P=0.07) and might be explained by the presence of antioxidants in white mushrooms which could have produced local protective effects in the gut. Strikingly, in black mushrooms and in white mushrooms supplemented with synthetic melanin groups, 60 and 75% of mice survived (P=0.002 and 0.001), respectively, up to day 45 when the experiment was terminated to perform the histological examination of their tissues (FIG. 5A). At the same time the white blood cell counts in black mushroom and in melanin-supplemented groups were not different from the non-irradiated controls (P=0.06) (FIG. 5B), while platelet counts were lower in both irradiated groups (P=0.03) (FIG. 5C), however, at the levels which ensure recovery in mice receiving radiation treatment (25). In lethally irradiated mice mortality results from damage to rapidly dividing tissues such as GI mucosa (26) and bone marrow suppression (27, 28). There were no signs of radiation damage in the stomachs, large and small intestines (LI and SI, respectively) in the surviving mice in black mushroom and melanin-supplemented groups (FIG. 5D-F). Bone marrow of irradiated mice had slight myeloid hyperplasia (FIG. 5G) and the spleens architecture was normal with some extramedullary hematopoesis (FIG. 5).

Figures 6A, 6B:
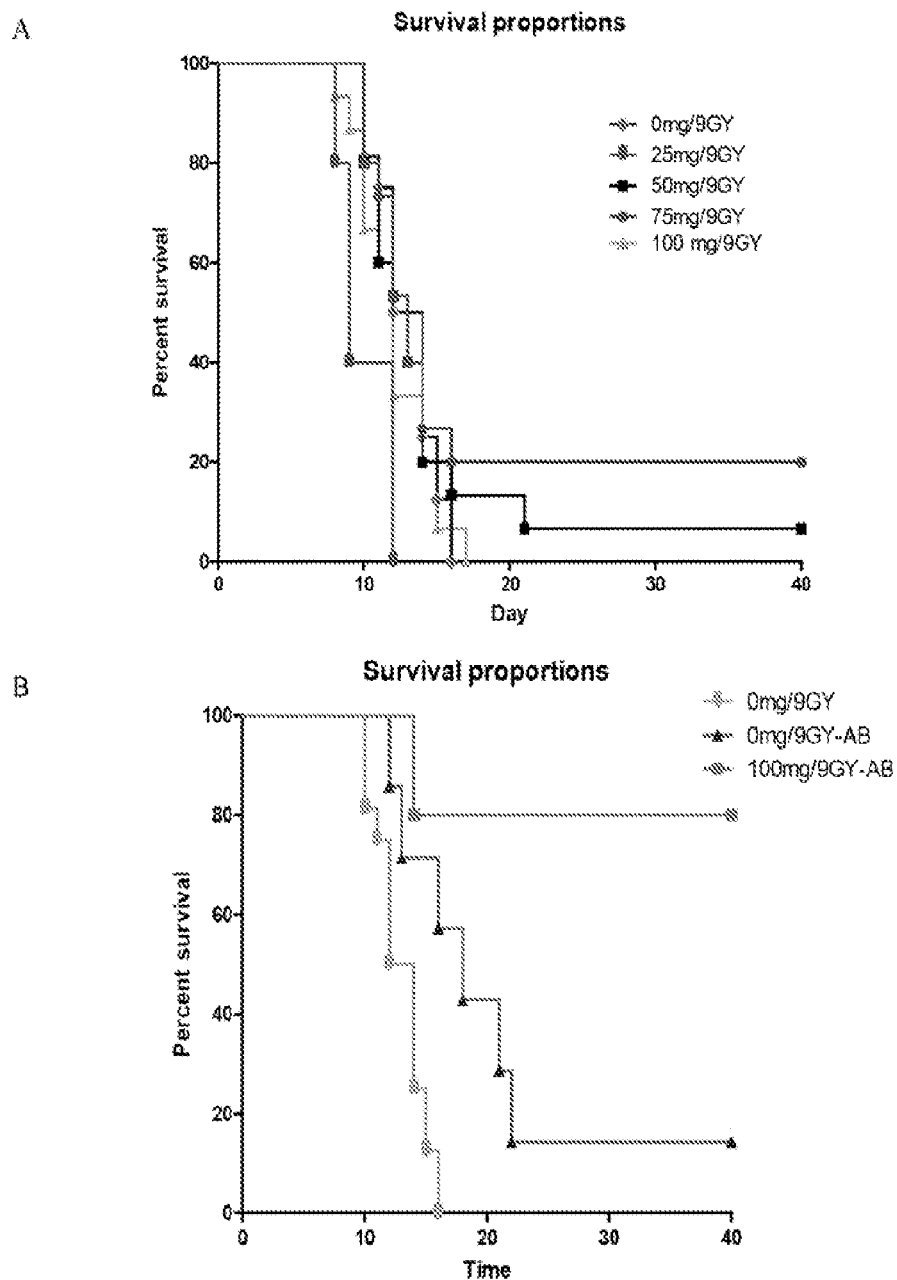
FIG. 6A-6D. Survival and weight change in CD-1 mice fed with different doses of synthetic pheomelanin and/or antibiotics and irradiated with 9 Gy gamma radiation at 2.5 Gy/min: a) mice fed with 0-100 mg/kg body weight pheomelanin; b) mice fed with 100 mg/kg pheomelanin followed by antibiotics for 5 days, or given PBS only, or given PBS followed by antibiotics for 5 days; c) combined results from a) and b); d) weight change in irradiated groups modeled using linear regression. AB—antibiotics.

Synthetic pheomelanin in combination with antibiotics protected the majority of mice against lethal dose of radiation. It was hypothesized that high linear attenuation coefficient and stable radical contents (18) of the synthetic pheomelanins would translate into radioprotection in mice. The dose response experiments demonstrated that orally administrated synthetic pheomelanin protected mice irradiated with 9 Gy at 2.5 Gy/min in a dose-dependent manner. Over a 40 day survival study, no protection was identified in mice receiving 25 mg/kg pheomelanin. Mice fed with 50 mg/kg had a 6.6% survival rate (P=0.02), while those receiving 75 mg/kg had a 20% survival rate (P=0.01) (FIG. 6A). However, no protection was observed when the pheomelanin dose was increased to 100 mg/kg (P=0.06). The possibility that the lack of protection at the higher melanin dose was a consequence of bowel-related effects that predisposed animals to bacterial sepsis was considered.

Figure 6C:
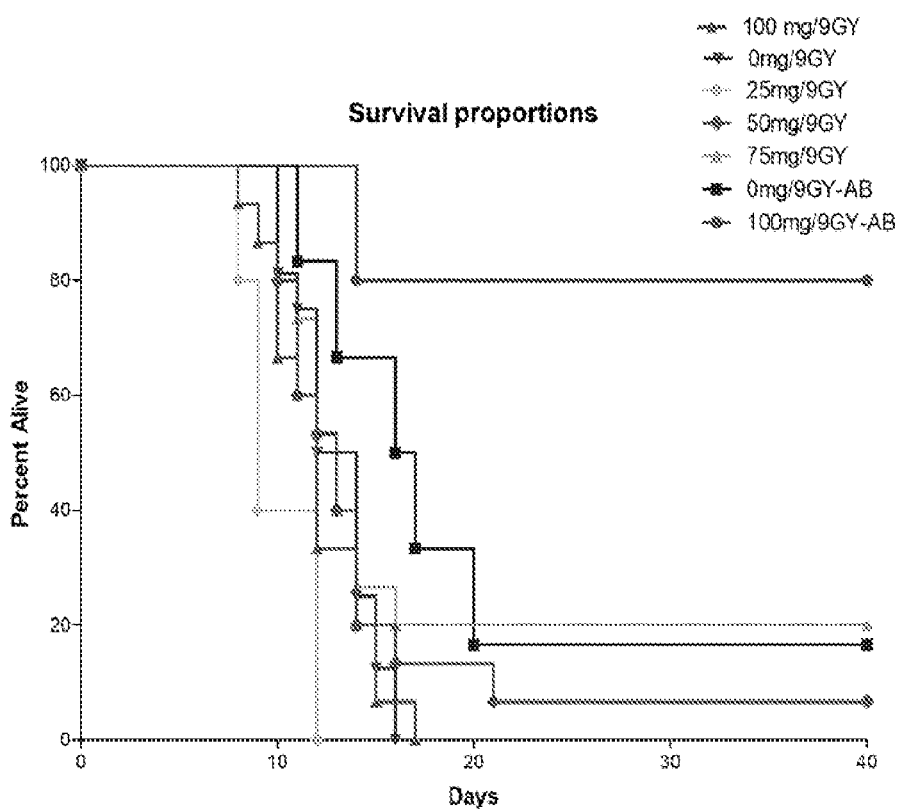

Hence, in a follow-up study, the effect of antimicrobial therapy on survival after pheomelanin administration and lethal irradiation was evaluated. Mice were given either PBS alone, or PBS in combination with antibiotics or 100 mg/kg pheomelanin in combination with antibiotics which resulted in 40 day survival of 0%, 16.7%, and 80% (P=0.005), respectively (FIG. 6B,6C).

Figure 6D:
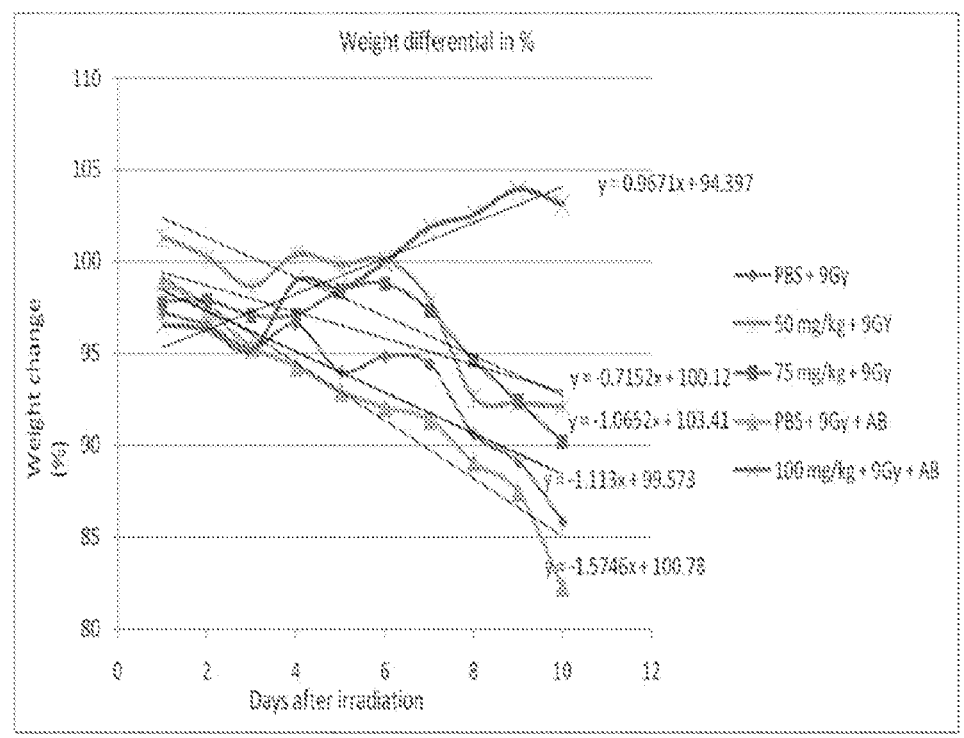

The rate of weight loss in the different treatments groups was analyzed by linear regression (FIG. 6D). The highest weight loss was observed in the groups given PBS alone or PBS in combination with antibiotics: a 1.6 and 1.1% decrease in total body weight per day, respectively. Mice given pheomelanin displayed significantly less weight loss when compared to PBS alone group: the group treated with 50 mg/kg of pheomelanin lost 1.0% of their body weight per day (P=0.02), while the group treated with 75 mg/kg had a 0.7% loss in body weight per day (P=0.015). Most importantly, mice receiving 100 mg/kg pheomelanin plus antibiotics actually gained weight at a rate of 1.0% per day after irradiation, a difference that was significant in comparison with all other groups (P<0.05).

Figure 7A:
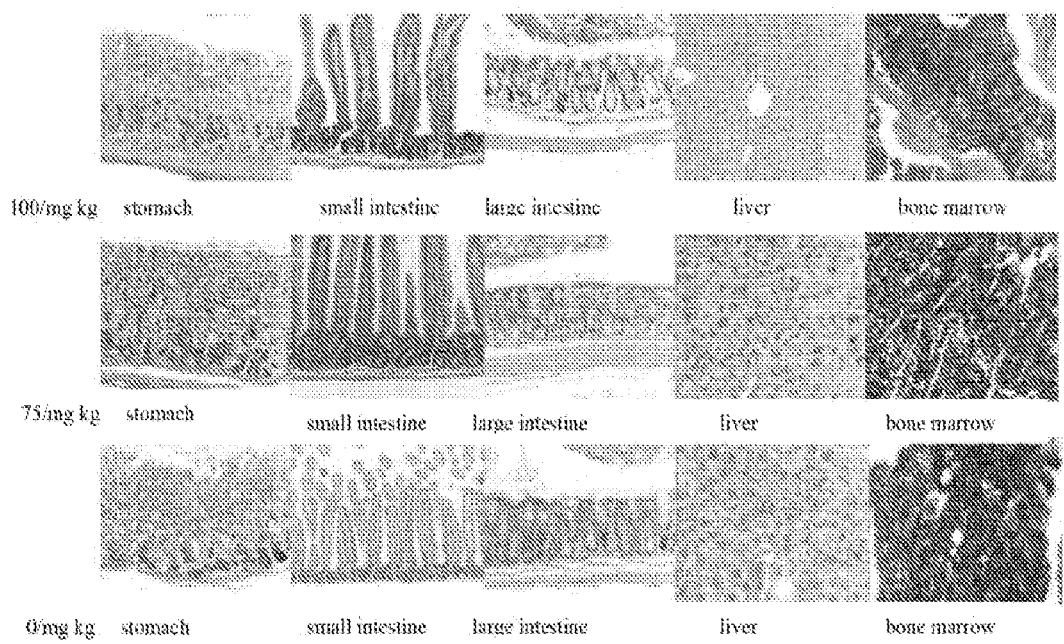
FIG. 7A-7C. Histological evaluation of the tissue in surviving mice post-irradiation with 9 Gy gamma radiation at 2.5 Gy/min: a) stomach, small intestine, large intestine, liver and bone marrow. Mice received 100 mg/kg pheomelanin plus antibiotics (upper row); 75 mg/kg pheomelanin (middle row); 0 mg/kg plus antibiotics (lower row); b) tissues from a mouse receiving 100 mg/kg pheomelanin plus antibiotics—focal microadenoma of the small intestine (left panel) and bone marrow (right panel); c) cecum of a single survivor in 0 mg/kg plus antibiotics group. The same region of the cecum is shown with magnification ×250 in the left panel, ×400 in the middle panel and ×1,000 in the right panel Each slide is a higher magnification of the same region. Magnification ×400 in a) and b).
Figure 7B:
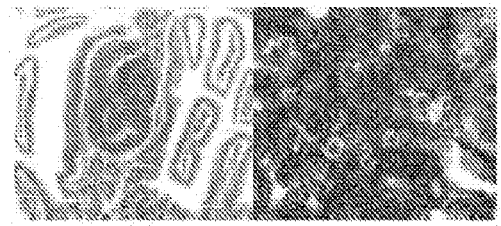
Figure 7C:
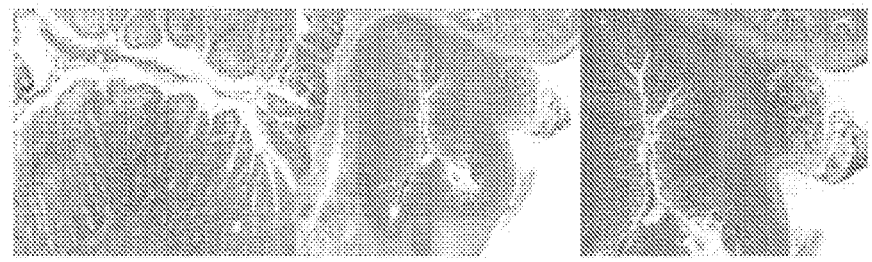

Histological evaluation of the tissue in surviving mice confirmed the body weight data by revealing no damage to the stomach, small intestine, large intestine, liver and bone marrow in surviving mice treated with 100 mg/kg pheomelanin plus antibiotics (FIG. 7A, upper row) or 75 mg/kg pheomelanin (FIG. 7A, middle row). Among the surviving mice in the 100 mg/kg pheomelanin plus antibiotics group (80% survival) only one mouse had a focal microadenoma in the small intestine (FIG. 7B, left panel) and moderately depleted bone marrow cellularity (FIG. 7B, right panel). The single survivor in PBS plus antibiotics group exhibited multifocal lymphohistiocytic and plasmacytic periportal infiltrates in the liver (FIG. 7A, lower row) and a focal perforation in the cecum with chronic active peritonitis (FIG. 7C).

Figure 8A:
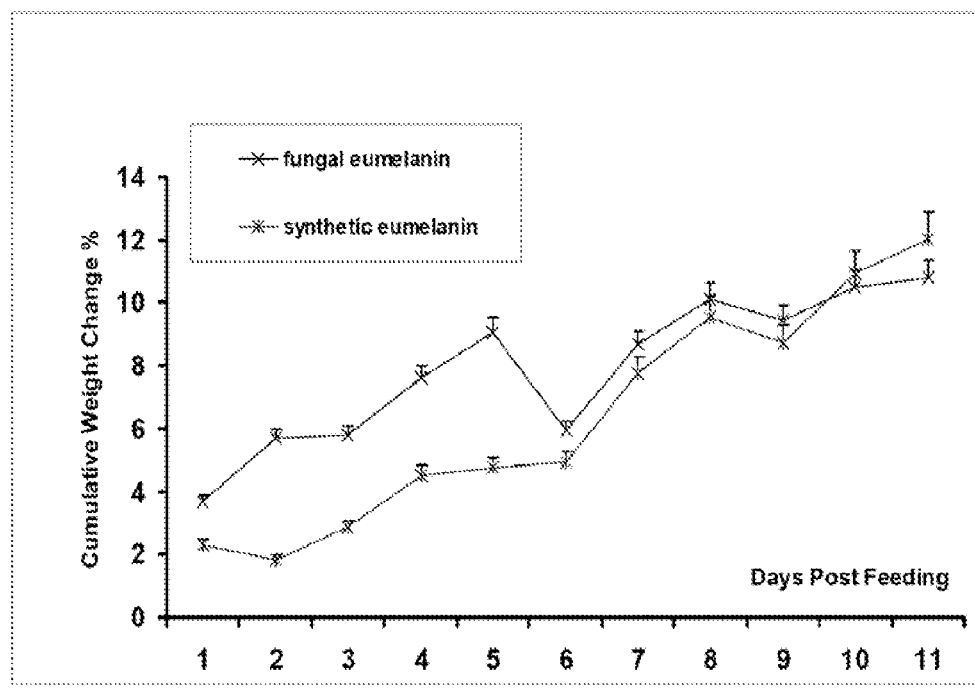
FIG. 8A-8B. Toxicity evaluation of microbial and synthetic eumelanin in non-irradiated CD-1 mice: a) body weight of mice fed with 15 mg/kg microbial or synthetic eumelanin; b) histology of GI organs from CD-1 mice fed with microbial eumelanin and sacrificed 24 hr later: left, stomach; middle, small intestine; right, colon. Original magnification ×400.
Figure 8B:
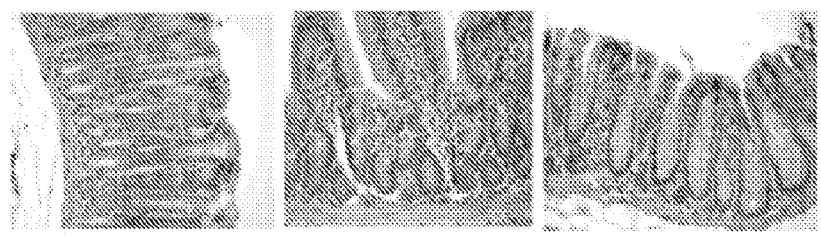

Microbial and synthetic eumelanins prolonged survival of lethally irradiated mice. Before carrying out irradiation studies we evaluated whether there was any toxicity associated with oral administration of microbial and synthetic melanins to CD-1 mice. Measures of toxicity were the body weight over 10 days and histological evaluation of gut tissue. Microbial and synthetic eu- and pheomelanins proved to be non-toxic with mice steadily gaining weight during the observation period which was confirmed by the normal histology of the gut (FIG. 8).

Encouraged by the lack of toxicity of microbial and synthetic melanins, the efficacy of orally administered synthetic and microbial eumelanins in protecting CD-1 mice against lethal irradiation was evaluated. Histological evaluation of GI tissues obtained from mice 4 hr post-irradiation with 9 Gy at 2.5 Gy/min from 137Cs source revealed that mice fed with microbial eumelanin had approximately 40% fewer apoptotic cells in stomach tissue than mice fed synthetic eumelanin or PBS (FIG. 10A-C). At 24 hr this trend continued with glandular cells being less attenuated in stomachs of mice fed with microbial eumelanin than in mice fed with synthetic eumelanin. Simultaneously, there were approximately 25% more mitotic figures and less apoptotic cells in both eumelanins groups in comparison with control PBS fed mice. In the small intestine there was no apparent difference between treatment groups. At 24 hr in the colonic glands of mice fed microbial eumelanin there was 30% less cellular reaction and apoptosis compared to the other colon samples (FIG. 9D-F).

Figure 9H:
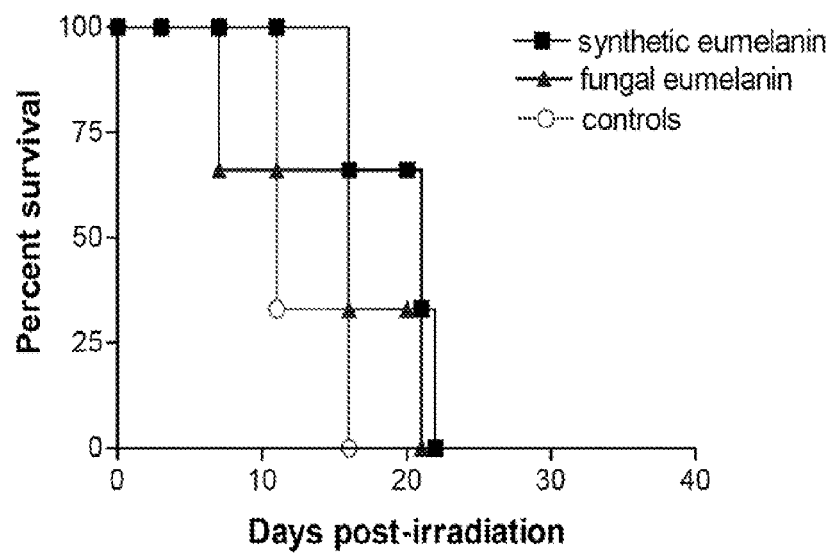

For the first four days post-irradiation, mice fed with microbial eumelanin lost slightly less weight than mice fed either PBS or synthetic eumelanin (FIG. 9G). By day 5, the cumulative weight loss in all groups had equalized and for the rest of the observation period the weight loss was the least pronounced in mice fed with synthetic eumelanin. The overall survival on day 11 post-irradiation was 100% in synthetic eumelanin group, 66% —in the microbial eumelanin group and 33% —in control mice fed with PBS, with the last mouse in this group dying on day 16 (FIG. 9J). For the duration of study, the mean survival for mice fed with microbial eumelanin was 13 d, for control PBS fed mice— 12.7 days and for synthetic eumelanin group—19 days (P=0.01, Mandel-Cox test).

Discussion

There is an ongoing and urgent need for oral radioprotectors that are inexpensive, do not require refrigeration for storage and transportation ("cold chain"), and are suitable for distribution to large numbers of people in the event of radiation emergencies such as the recent nuclear accident at Fukushima-Daiichi nuclear plants. This need is enhanced by the fact that many developing nations are considering increased reliance on nuclear power as an alternative to fossil fuels and that a major expansion in nuclear programs carries significant risks as evidenced by two major accidents at Chernobyl and Fukushima-Daiichi in the space of one generation. One potential radioprotector that has been studied extensively is amifostine (28-30). It belongs to the class of free radical scavengers that includes aminothiols and phosphorothioates, and is administered as a prodrug that must be metabolized to an active form to be effective. While this drug has some radioprotective efficacy, it also has several undesirable properties, including a relatively low radioprotective capacity, potentially serious side effects such as anaphylaxis and the need for intravenous administration. In a study by Burdelya et al. (31), a different approach to radioprotection was taken by pharmacologically suppressing apoptosis in the irradiated cells. This was done by pretreating experimental animals with flagellin-derived polypeptide which binds to Toll-like receptor 5 and activates nuclear factor-κB signaling. While this method showed some promise, the drug also has to be given parenterally and might have carcinogenic side effects by virtue of interfering with the process of apoptosis.

Herein, in vivo studies were conducted to evaluate protective effect of different types of orally administered melanins on the GI tract in mice receiving a lethal dose of 9 Gy at a high dose rate. The radioprotective effects of melanin are proposed to be based on controlled dissipation of Compton electron energy by melanin which results in a decreased number of interactions between Compton electrons and cellular milieu and the scavenging of free reactive radicals by melanin (18). The protective effects of two eumelanins— microbial eumelanin purified from C. neoformans and commercially available synthetic eumelanin were compared. Histological examination of the stomachs and colons of the irradiated mice revealed that the mice given microbial eumelanin were better protected than those given synthetic eumelanin or controls. However, this early protective effect of microbial eumelanin did not extend into the long-term protection while synthetic eumelanin administration resulted in statistically significant prolongation in survival. This surprising observation may be explained by the inflammation which microbial eumelanin can cause in the mucosa due to the persistent presence of immunogenic proteins and polysaccharides intertwined with its structure even after rigorous multi-step purification (32). Melanin 'ghosts' derived from melanized fungal cells contain cell wall components which are known to be highly immunogenic. For example, zymosan particles prepared from yeast cell wall are notoriously pro-inflammatory (33) and *C. neoformans*-derived melanin have been shown to trigger direct inflammation (34). Such inflammation might increase the damage sustained from radiation and be accompanied by edema which could explain the less significant weight loss in the microbial eumelanin group in comparison with the synthetic eumelanin and control groups during the first four days after irradiation. The synthetic eumelanin afforded statistically significant prolongation in survival for the overall duration of experiment, which provided impetus for further investigation of its role in radioprotection by orally administering to mice synthetic pheomelanin which has higher number of stable free radicals than eumelanin and was more radioprotective in vitro (18).

Pheomelanin protected mice in a dose-dependent manner in the dose range of 25-75 mg/kg body weight. Since the 100 mg/kg dose did not protect mice, it was hypothesized that the higher dose of melanin may have had unanticipated adverse effects in damaged tissue. To explore the contribution of associated bacteremia to the mortality antibiotics were administered to mice post-irradiation. Antibiotic administration resulted in 80% survival of irradiated mice treated with 100 mg/kg pheomelanin. When compared to published data—pheomelanin plus antibiotics was more protective then amifostine (60% survival after 9 Gy delivered at 1 Gy/min (17)), and equal to flagellin-derived polypeptide (80% survival after 9 Gy delivered at 2.3 Gy/min (20)). The increase in radiation dose rate is known to make the cellular repair mechanisms less efficient (35). The histological evaluation of the surviving mice in groups protected with pheomelanin alone or with pheomelanin and antibiotics revealed no obvious radiation damage to the major organs. Among the survivors in the group receiving 100 mg/kg pheomelanin plus antibiotics only one mouse had any abnormality in its major organs, which consisted of a moderate depletion of the bone marrow and an isolated microadenoma of the small intestine. These abnormalities may or may not reflect the effect of irradiation. In contrast, the single survivor in the antibiotics only group had focal typhlitis and perforation associated with peritonitis. Ionizing radiation induces disruption of the mucosal integrity which is often complicated by ulceration (26, 36). Focal ulcerations are common; these vary from simple loss of epithelial layer with acute inflammation of the lamina propria to ulcers that may penetrate to varying depths of the intestinal wall, even to the serosa. A perforated appendix and associated peritonitis is a frequent clinical consequence of exposure to ionizing radiation in patients (26). It was concluded that the cecal perforation was a result of radiation injury, and the mouse survived until the end of the study due to antibiotic administration, which prevented fatal peritonitis.

The ideal radioprotective agent would both be protective and cost-effective. Black edible mushrooms, in their native form, provide a natural radioprotector that is readily available. The equal survival of mice protected with either black mushrooms or white mushrooms supplemented with melanin establishes the causality between the presence of melanin in black mushrooms and their radioprotective properties. Interestingly, approximately the same percentage of mice survived in experiments with mushrooms when no antibiotics were given as in the experiment with the synthetic pheomelanin where the supplementation with antibiotics was required for the protection. This effect is most likely due to the combination of melanin and soluble antioxidants which are present in mushrooms (FIG. 2). Given that a significant proportion of black mushroom- or white mushroom-supplemented with melanin-fed mice became long term survivors it must follow that the presence of melanin in the GI tract provided local protection that allowed these mice to recover. Protection of GI mucosa would prevent death by a GI syndrome and sepsis. Hence, local GI protection appears to translate into systemic protection and this observation establishes a new concept in the approach to protecting against radiation sickness. Black edible mushrooms could be prepared as a suspension in a palatable liquid and distributed as food supplement to affected populations. This radioprotection may also benefit cancer patients undergoing radiation treatment, as radiation-induced injury to the GI tract is common in patients undergoing external radiation beam therapy (EBRT).

Materials and Methods

Melanin sources and physico-chemical analyses. Commercial synthetic eumelanin made from tyrosine was obtained from Sigma-Aldrich. The microbial eumelanin from *C. neoformans* strain 24067 in form of "ghosts" (hollow melanin spheres from which all cellular contents has been removed via multi-step purification procedure) was purified as previously described8. Synthetic pheomelanin using 5-S-cysteinyldopa was produced by incubating 0.5 mmol 5-S-cysteinyldopa with 0.025 mmol L-DOPA, added as a catalyst, in 0.05 M sodium phosphate buffer, pH 6.8 and with mushroom tyrosinase (Sigma) in the amount of 8300 units (773 µL of 2 mg/mL solution) with constant agitation overnight at 37° C. After the overnight incubation, the oxidation reaction was halted by the addition of 250 µL 6 M HCl to lower the pH to approximately 3.0. This acidified mixture was kept at 2° C. for 1 hour. The precipitate was collected by centrifugation, washed three times with 15 mL 1% acetic acid, washed twice with 15 mL acetone, once more with 15 mL 1% acetic acid, and re-suspended in de-ionized water. The resulting pheomelanin was then lyophilized and suspended in PBS at a concentration of 12.5 mg/mL to create the stock suspension.

Dried *Auricularia auricula-judae* (black mushrooms) and *Boletus edulis* (white mushrooms) were purchased from Trader Joe's (Monrovia, Calif.). Melanin from black mushrooms was purified as described previously (19). Elemental analysis of melanin was carried out by QTI (Whitehouse, N.J.). EPR of dried mushrooms and oxidative HPLC of melanin using permanganate oxidation were performed as in (18). The antioxidant capacity of methanol extracts from black and white mushrooms in DPPH assay was measured as in (23).

Evaluation of potential toxicity of melanins. All animal studies were carried out in accordance with the guidelines of the Albert Einstein College of Medicine Animal Care and Use Committee. Six-eight weeks old CD-1 female mice (Charles River Breeding Laboratories, Portage, Mich.) were used in all experiments. Mice were divided into groups of five and fed 15 mg/kg body weight either synthetic or microbial eumelanins, or 100 mg/kg synthetic pheomelanin or PBS via gavage needle. Mice were evaluated daily for body weight and their physical condition. Two mice per group were humanely sacrificed at 24 hr post-feeding with melanin, and the remaining mice were sacrificed at day 14. The stomach and small and large intestines were fixed in 10% neutral buffered formalin and routinely processed for paraffin embedding. Samples were sectioned to 5 μm and stained with hematoxylin and eosin (H&E) for histological evaluation.

Imaging. The in vivo imaging was performed with IVIS Spectrum Imaging System (Caliper Life Sciences, Hopton, Mass.) in epifluorescence mode equipped with 675/30 nm and 840/20 nm filters for excitation and emission, respectively. Mice were fed with non-fluorescent chow for 5 days and then fasted overnight before the imaging experiment to exclude the interference from the remnant autofluorescence of the chow. They were given 1 g/kg body weight white mushrooms suspension in water via gavage needle and imaged in supine position under Isoflurane anesthesia at 15, 30 and 60 min post-feeding.

In vivo radioprotection with various melanins. Microbial and synthetic eumelanins. CD-1 mice (13 mice per group) were fed either synthetic eumelanin or microbial eumelanin or PBS via gavage needle at a dose of 15 mg/kg body weight. One hour post-eumelanin feeding the mice were subjected to whole body irradiation in a 137-Cs irradiator with a total body dose of 9 Gy delivered at 2.5 Gy/min. At 4 and 24 hr, 2 mice per group were humanely sacrificed and their stomachs, small intestine and colon were removed and processed as previously described. The remaining animals were monitored until death with daily measurements of body weight. Moribund animals were humanely euthanized.

Synthetic pheomelanin. CD-1 mice were divided into 5 groups of fifteen mice. The groups were treated with 0, 25, 50, 75, 100 mg/kg melanin suspension in PBS via gavage. One hr post feeding the mice were subjected to whole body irradiation in a 137-Cs irradiator with a total body dose of 9 Gy delivered at 2.5 Gy/min and their body weight and survival were monitored for 40 days. The rate of weight change was quantified by using a linear regression analysis (Prism, GraphPad, San Diego, Calif.). In a follow-up study mice were divided into three groups. Group 1 was treated by oral gavage with 100 mg/kg melanin suspension in PBS and group 2 and 3 were treated by oral gavage with only PBS followed by irradiation as above of all three groups. Starting at 2 days after irradiation groups 1 and 2 were dosed subcutaneously with penicillin (10,000 units/mL) and streptomycin (10 mg/mL) (Sigma, St. Louis, Mo.) at 120 μL twice a day for 5 days. At the completion of the study on day 40, all surviving mice were sacrificed and their stomachs, small intestine, large intestine, liver, sternum and femur were removed and processed as previously described for histological evaluation.

Black mushrooms. Since dried black mushroom contain 10% melanin, black mushrooms were administered as suspension in sterile PBS via gavage as 1 g/kg body weight dose to match the melanin concentrations in the described above experiments with pure synthetic melanins. CD-1 mice were divided into groups of 5-6 and fed 1 g/kg body weight black mushroom suspension in PBS, or PBS alone, or 1 g/kg white mushroom suspension, or 1 g/kg white mushroom suspension supplemented with 100 mg/kg synthetic melanin via gavage needle. One hour after mushroom administration mice were irradiated with 9 Gy dose of Cs-137 radiation at a dose rate of 2.5 Gy/min. Mice were evaluated daily for body weight and their physical condition for 45 days. The experiment was performed twice. At the conclusion of the experiment the surviving mice were humanely sacrificed, their blood chemistry was analyzed for white blood cells and platelet count, gross pathology was performed and the stomach, small and large intestines, spleen and bone marrow were subjected to histological evaluation. Survival of mice was analyzed using log-rank test, the WBC and platelet counts—by one tail Student's test. The differences in results were considered statistically significant when P was <0.05.

REFERENCES

1) Dadachova E, Bryan R A, Huang X, Moadel T, Schweitzer A D, Aisen P, Nosanchuk J D, and Casadevall A. Ionizing radiation changes the electronic properties of melanin and enhances the growth of melanized fungi. PLoS One 5:e457 (2007).
2) Dadachova E., Bryan R. A., Howell R. C., Schweitzer A. D., Aisen P., Nosanchuk J. D., and Casadevall A. Radioprotective properties of melanin are a function of its chemical composition, free stable radical presence and spatial arrangement. Pigment Cell Melanoma Res. 21(2):192-9 (2008).
3) Schweitzer A., R. C. Howell, Z. Jiang, R. A Bryan, G. Gerfen, C-C. Chen, D. Mah, S. Cahill, A. Casadevall, and E. Dadachova. Physico-chemical evaluation of rationally designed melanins as novel nature-inspired radioprotectors. PLOS ONE 4(9): e7229 (2009).
4) Schweitzer A. D., E. Revskaya, P. Chu, V. Pazo, M. Friedman, J. D. Nosanchuk, S. Cahill, S. Frases, A. Casadevall, and E. Dadachova Melanin-covered nanoparticles for protection of bone marrow during radiation therapy of cancer. Intern. J. Rad. Oncol. Biol. Physics. 78(5):1494-502 (2010).
5) Hill, H. Z. The function of melanin or six blind people examine an elephant. *Bioessays* 14: 49-56 (1992).
6) Jacobson, E. S. 2000. Pathogenic roles for fungal melanins. *Clin. Microbiol. Rev.* 13:708-717.
7) Bonner, T. G., A. Duncan. 1962. Infra-red spectra of some melanins. *Nature* 194:1078-1079.
8) Chaskes, S. and R. L. Tyndall. 1975. Pigment production by *Cryptococcus neoformans* from para- and ortho-diphenols: effect of the nitrogen source. *J. Clin. Microbial.* 1:509-514.
9) Chaskes, S. and R. L. Tyndall. 1978. Pigment production by *Cryptococcus neoformans* and other *Cryptococcus* species from aminophenols and diaminobenzenes. *J. Clin. Microbiol.* 7:146-152.
10) Chaskes, S. and R. Tyndall. 1978. Pigmentation and autoflourescence of *cryptococcus* species after growth on tryptophan and anthranilic acid media. *Mycopathologia* 64:105-112.
11) Wang, Y., Aisen, P., and Casadevall, A. Melanin, melanin "ghosts" and melanin composition in *Cryptococcus neoformans*. *Infec. Immun.* 64: 2420-2424 (1996).
12) Hill H Z (1992) The function of melanin or six blind people examine an elephant. Bioessays 14:49-56.
13) Dadachova E, Casadevall A (2008) Ionizing radiation: how fungi cope, adapt, and exploit with the help of melanin. Curr Opinion Microbiol 11:1-7.
14) Dadachova E et al. (2007) Ionizing radiation changes the electronic properties of melanin and enhances the growth of melanized fungi. PLoS ONE 5:e457.
15) Dadachova E et al. (2008) Radioprotective properties of melanin are a function of its chemical composition, free stable radical presence and spatial arrangement. Pigment Cell Melanoma Res 21:192-9.
16) Khajo A, et al. (2011) Protection of melanized *Cryptococcus neoformans* from lethal dose gamma irradiation involves changes in melanin's chemical structure and paramagnetism. PLoS ONE 6: e25092.
17) Turick C E, Ekechukwu A A, Milliken C E, Casadevall A, Dadachova E (2011) Gamma Radiation Interacts with Melanin to Alter its Oxidation-Reduction Potential and Results in Electric Current Production. Bioelectrochem [Epub ahead of print].

18) Schweitzer A et al. (2009) Physico-chemical evaluation of rationally designed melanins as novel nature-inspired radioprotectors. PLOS ONE 4: e7229.

19) Wang Y, Aisen P, Casadevall A (1996) Melanin, melanin "ghosts" and melanin composition in *Cryptococcus neoformans*. Infec Immun 64: 2420-2424.

20) Ito S, Fujita K (1985) Microanalysis of eumelanin and pheomelanin in hair and melanomas by chemical degradation and liquid chromatography. Anal Biochem 144:527-536.

21) Wakamatsu K, Ito S (2002) Advanced chemical methods in melanin determination. Pigment Cell Res 15:174-183.

22) Starratt A N, Ross L M, Lazarovits G (2002) 1,8-Dihydroxynaphthalene monoglucoside, a new metabolite of Sclerotinia sclerotiorum, and the effect of tricyclazole on its production. Can J Microbiol 48:320-325.

23) Kho Y S, Vikineswary S, Abdullah N, Kuppusamy U R, Oh H I (2009) Antioxidant capacity of fresh and processed fruit bodies and mycelium of *Auricularia auricula-judae* (Fr.) Quél. J Med Food 12:167-74.

24) Enochs W S, Nilges M J, Swartz H M (1993) The standardized test for the identification and characterization of melanins using electron paramagnetic (EPR) spectroscopy. Pigment Cell Res 6:91-99.

25) Behr T M et al. (1999) High-linear energy transfer (LET) alpha versus low-LET beta emitters in radioimmunotherapy of solid tumors: therapeutic efficacy and dose-limiting toxicity of 213Bi-versus 90Y-labeled CO17-1A Fab' fragments in a human colonic cancer model. Cancer Res 59:2635-43.

26) Somosy Z. Horvath G, Telbisz A, Rez G, Pallia Z (2002) Morphological aspects of ionizing radiation response of small intestine. Micron 33: 167-178.

27) Li H et al. (2011) Mn(III) meso-tetrakis-(N-ethylpyridinium-2-yl) porphyrin mitigates total body irradiation-induced long-term bone marrow suppression. Free Radic Biol Med [Epub ahead of print].

28) Pamujula S et al. (2005) Radio-protection in mice following oral delivery of amifostine nanoparticles. Int J Radiat Biol 81:251-257.

29) Small W, Jr (2003) Radiation. Therapy Oncology Group C-0116 trial. Cytoprotection/radioprotection with amifostine: potential role in cervical cancer and early findings in the Radiation Therapy Oncology Group C-0116 trial. Semin Oncol 30(6 Suppl 18):68-71.

30) Menard C at al. (2003) Clinical trial of endorectal amifostine for radioprotection in patients with prostate cancer: rationale and early results. Semin Oncol 30(6 Suppl 18):63-7.

31) Burdelya L G et al. (2008) An agonist of toll-like receptor 5 has radioprotective activity in mouse and primate models. Science 320:226-30.

32) Zhong J, Frases S, Wang H, Casadevall A, Stark R E (2008) Following fungal melanin biosynthesis with solid-state NMR: biopolymer molecular structures and possible connections to cell-wall polysaccharides. Biochemistry 47: 4701-4710.

33) Sato M et al. (2003) Direct binding of Toll-like receptor 2 to zymosan, and zymosan-induced NF-kappa B activation and TNF-alpha secretion are down-regulated by lung collectin surfactant protein A. J Immunol 171 (1): 417-25.

34) Mednick A J, Nosanchuk J D, Casadevall A (2000) Melanization of *Cryptococcus neoformans* affects lung inflammatory responses during cryptococcal infection. Infect Immun 73(4):2012-9.

35) Hall E J (2000) in Radiobiology for the Radiologist (Lippincott Williams & Willkins, Philadelphia), pp 91-94.

36) Berthrong M, Fajardo L F (1981) Radiation injury in surgical pathology. Part II. Alimentary tract. Amer J Surgical Pathol 5: 153-178.

What is claimed is:

1. A method of reducing radiation damage from a computer tomography (CT) scan of a subject comprising administering an agent for computer tomography comprising a drinkable suspension containing at least 250 mg of a dried powdered edible source of melanin in a volume of at least 10 mL to the subject prior to the CT scan.

2. The method of claim 1, wherein the edible source of melanin comprises *Auricularia auricular-judae*.

3. The method of claim 1, wherein the CT scan is a high resolution multi-slice CT scan.

\* \* \* \* \*